(12) United States Patent
Nougairéde et al.

(10) Patent No.: US 10,619,137 B2
(45) Date of Patent: Apr. 14, 2020

(54) METHOD FOR RAPID GENERATION OF AN ATTENUATED RNA VIRUS

(71) Applicants: UNIVERSITÉ D'AIX-MARSEILLE, Marseilles (FR); INSERM, Paris (FR)

(72) Inventors: Antoine Nougairéde, Marseilles (FR); Lauriane De Fabritus, Marseilles (FR); Fabien Aubry, Marseilles (FR); Xavier De Lamballerie, Ensués la Redonne (FR); Ernest Andrew Gould, St Albans (GB)

(73) Assignees: UNIVERSITÉ D'AIX-MARSEILLE, Marseilles (FR); INSERM, Paris (FR)

( * ) Notice: Subject to any disclaimer, the term of this patent is extended or adjusted under 35 U.S.C. 154(b) by 0 days.

(21) Appl. No.: 15/315,687

(22) PCT Filed: Jun. 19, 2015

(86) PCT No.: PCT/EP2015/063815
§ 371 (c)(1),
(2) Date: Dec. 1, 2016

(87) PCT Pub. No.: WO2015/193473
PCT Pub. Date: Dec. 23, 2015

(65) Prior Publication Data
US 2018/0201908 A1    Jul. 19, 2018

(30) Foreign Application Priority Data
Jun. 20, 2014  (EP) .................................... 14305956

(51) Int. Cl.
| | |
|---|---|
| *C12N 7/04* | (2006.01) |
| *A61K 39/12* | (2006.01) |
| *C12N 7/00* | (2006.01) |
| *C12N 15/10* | (2006.01) |
| *A61K 39/00* | (2006.01) |

(52) U.S. Cl.
CPC ................ *C12N 7/04* (2013.01); *A61K 39/12* (2013.01); *C12N 7/00* (2013.01); *C12N 15/1031* (2013.01); *A61K 2039/525* (2013.01); *A61K 2039/5254* (2013.01); *C12N 2770/24051* (2013.01); *C12N 2770/24151* (2013.01); *Y02A 50/383* (2018.01); *Y02A 50/39* (2018.01); *Y02A 50/396* (2018.01)

(58) Field of Classification Search
None
See application file for complete search history.

(56) References Cited

PUBLICATIONS

Nougairede, A. et al. "Random Codon Re-encoding Induces Stable Reduction of Replicative Fitness of Chikungunya Virus in Primate and Mosquito Cells", Plos Pathogens, vol. 9 No. 2, Feb. 21, 2013.
Nougairede, A. et al. "Supporting Information: Text S1", Feb. 21, 2013, XP055149137, DOI: 10.1371/journal.ppat.1003172.s002.
Nougairede, A. et al. "Supporting Information: Text S2", Feb. 21, 2013, XP055149139,D DPO: 10.1371/journal.ppat.1003172.s003.
Siridechadilok B., et al. "A Simplified Positive-Sense-RNA Virus Construction Approach that Enhances Analysis Throughput" Journal of Virology, vol. 87, No. 23, Dec. 1, 2013.
Aubry, F. et al. "Single-estranded positive-sense RNA viruses generated in days using infectious subgenomic amplicons", Journal of General Virology, vol. 95, No. Pt 11, Jul. 22, 2014.
De Fabritus L. et al. "Attenuation of Tick-Borne Encephalitis Virus Using Large-Scale Random Codon Re-encoding", Plos Pathogens, vol. 11, No. 3, Mar. 3, 2015.

*Primary Examiner* — Stacy B Chen
(74) *Attorney, Agent, or Firm* — McAndrews, Held & Malloy, Ltd.

(57) ABSTRACT

The present invention harnesses the power of mutagenesis to produce an attenuated RNA virus in a very short period, i.e. as soon as the complete sequence of the target virus is known and an infectious genome can be produced.

13 Claims, 2 Drawing Sheets
Specification includes a Sequence Listing.

Figure 1

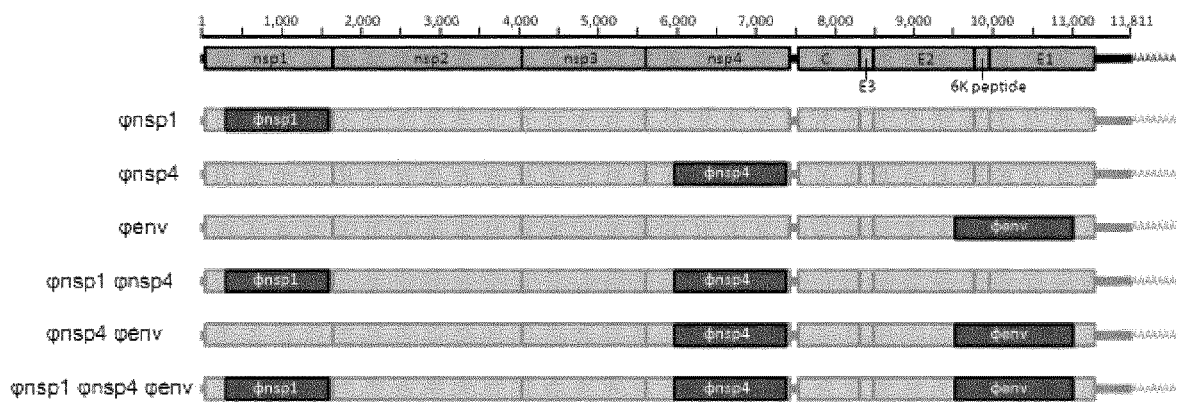
Figure 2
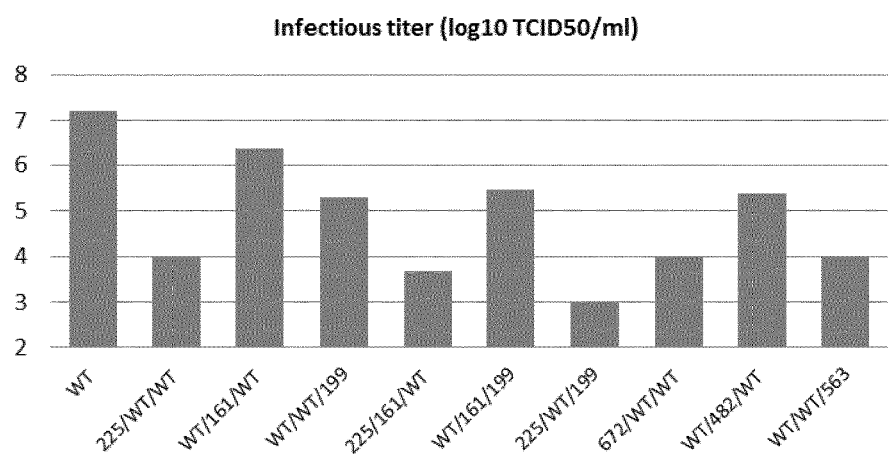
Figure 3
Figure 4

SEQUENCE LISTING

```
<160> NUMBER OF SEQ ID NOS: 72

<210> SEQ ID NO 1
<211> LENGTH: 781
<212> TYPE: DNA
<213> ORGANISM: Artificial Sequence
<220> FEATURE:
<223> OTHER INFORMATION: Promotor

<400> SEQUENCE: 1
gaataagggc gacacggaaa tgtcacccaa ctgatcttca gcatcttcaa tattggccat      60
tagccatatt attcattggt tatatagcat aaatcaatat tggctattgg ccattgcata     120
cgttgtatct atatcataat atgtacattt atattggctc atgtccaata tgaccgccat     180
gttggcattg attattgact agttattaat agtaatcaat tacggggtca ttagttcata     240
gcccatatat ggagttccgc gttacataac ttacggtaaa tggcccgcct ggctgaccgc     300
ccaacgaccc ccgcccattg acgtcaataa tgacgtatgt tcccatagta acgccaatag     360
ggactttcca ttgacgtcaa tgggtggagt atttacggta aactgcccac ttggcagtac     420
atcaagtgta tcatatgcca agtccgcccc ctattgacgt caatgacggt aaatggcccg     480
cctggcatta tgcccagtac atgaccttac ggactttcc tacttggcag tacatctacg     540
tattagtcat cgctattacc atggtgatgc ggttttggca gtacaccaat gggcgtggat     600
agcggtttga ctcacgggga tttccaagtc tccaccccat tgacgtcaat gggagtttgt     660
tttggcacca aaatcaacgg gactttccaa aatgtcgtaa taacccccgcc ccgttgacgc     720 aaatgggcgg taggcgtgta cggtgggagg tctatataag cagagctcgt ttagtgaacc     780
g                                                                      781

<210> SEQ ID NO 2
<211> LENGTH: 192
<212> TYPE: DNA
<213> ORGANISM: Artificial Sequence
<220> FEATURE:
<223> OTHER INFORMATION: HDR - SV40pA

<400> SEQUENCE: 2
ggccggcatg gtcccagcct cctcgctggc gccggctggg caacattccg aggggaccgt      60
cccctcggta atggcgaatg ggactcgcga cagacatgat aagatacatt gatgagtttg     120
gacaaaccac aactagaatg cagtgaaaaa aatgctttat ttgtgaaatt aagcgctggc     180
attgaccctg ag                                                          192

<210> SEQ ID NO 3
<211> LENGTH: 23
<212> TYPE: PRT
```

```
<213> ORGANISM: Artificial Sequence
<220> FEATURE:
<223> OTHER INFORMATION: primer F

<400> SEQUENCE: 3

Cys Ala Cys Cys Cys Ala Ala Cys Thr Gly Ala Thr Cys Thr Thr Cys
1               5                   10                  15

Ala Gly Cys Ala Thr Cys Thr
            20

<210> SEQ ID NO 4
<211> LENGTH: 25
<212> TYPE: DNA
<213> ORGANISM: Artificial Sequence
<220> FEATURE:
<223> OTHER INFORMATION: primer R

<400> SEQUENCE: 4
gaagaatgat tctgtaagtg tccag                                      25

<210> SEQ ID NO 5
<211> LENGTH: 22
<212> TYPE: DNA
<213> ORGANISM: Artificial Sequence
<220> FEATURE:
<223> OTHER INFORMATION: primer F

<400> SEQUENCE: 5
cgttgccatg ccaatcttag cg                                         22

<210> SEQ ID NO 6
<211> LENGTH: 22
<212> TYPE: DNA
<213> ORGANISM: Artificial Sequence
<220> FEATURE:
<223> OTHER INFORMATION: primer R

<400> SEQUENCE: 6
ggtgcttgcg tccttccacc aa                                         22

<210> SEQ ID NO 7
<211> LENGTH: 25
<212> TYPE: DNA
<213> ORGANISM: Artificial Sequence
<220> FEATURE:
<223> OTHER INFORMATION: primer F

<400> SEQUENCE: 7
caaatgagta tggaatgctg gaaaa                                      25

<210> SEQ ID NO 8
<211> LENGTH: 22
<212> TYPE: DNA
<213> ORGANISM: Artificial Sequence
<220> FEATURE:
<223> OTHER INFORMATION: primer R

<400> SEQUENCE: 8
ctcagggtca atgccagcgc tt                                         22

<210> SEQ ID NO 9
<211> LENGTH: 20
<212> TYPE: DNA
<213> ORGANISM: Artificial Sequence
<220> FEATURE:
<223> OTHER INFORMATION: primer F
```

```
<400> SEQUENCE: 9
gcccaccgga aggagctgac                                              20

<210> SEQ ID NO 10
<211> LENGTH: 23
<212> TYPE: DNA
<213> ORGANISM: Artificial Sequence
<220> FEATURE:
<223> OTHER INFORMATION: primer R

<400> SEQUENCE: 10
cagagagcaa atccctatga cga                                          23

<210> SEQ ID NO 11
<211> LENGTH: 22
<212> TYPE: DNA
<213> ORGANISM: Artificial Sequence
<220> FEATURE:
<223> OTHER INFORMATION: primer F

<400> SEQUENCE: 11
cgtcaccatg ccagtcttag cg                                           22

<210> SEQ ID NO 12
<211> LENGTH: 22
<212> TYPE: DNA
<213> ORGANISM: Artificial Sequence
<220> FEATURE:
<223> OTHER INFORMATION: primer R

<400> SEQUENCE: 12
gcttggcaat ccagtcagtc ct                                           22

<210> SEQ ID NO 13
<211> LENGTH: 24
<212> TYPE: DNA
<213> ORGANISM: Artificial Sequence
<220> FEATURE:
<223> OTHER INFORMATION: primer F

<400> SEQUENCE: 13
caaacgagta cggaatgcta gaaa                                         24

<210> SEQ ID NO 14
<211> LENGTH: 24
<212> TYPE: DNA
<213> ORGANISM: Artificial Sequence
<220> FEATURE:
<223> OTHER INFORMATION: primer R

<400> SEQUENCE: 14
ctcatgtttg acagcttatc atcg                                         24

<210> SEQ ID NO 15
<211> LENGTH: 26
<212> TYPE: DNA
<213> ORGANISM: Artificial Sequence
<220> FEATURE:
<223> OTHER INFORMATION: primer F

<400> SEQUENCE: 15
tcaatattgg ccattagcca tattat                                       26

<210> SEQ ID NO 16
```

```
<211> LENGTH: 24
<212> TYPE: DNA
<213> ORGANISM: Artificial Sequence
<220> FEATURE:
<223> OTHER INFORMATION: Primer R

<400> SEQUENCE: 16
tggattgaac actcctgtag acgc                                            24

<210> SEQ ID NO 17
<211> LENGTH: 23
<212> TYPE: DNA
<213> ORGANISM: Artificial Sequence
<220> FEATURE:
<223> OTHER INFORMATION: primer F

<400> SEQUENCE: 17
tggttggagt tggaagcctc atc                                             23

<210> SEQ ID NO 18
<211> LENGTH: 19
<212> TYPE: DNA
<213> ORGANISM: Artificial Sequence
<220> FEATURE:
<223> OTHER INFORMATION: primer R

<400> SEQUENCE: 18
gaccatgccg tggccggcc                                                  19

<210> SEQ ID NO 19
<211> LENGTH: 24
<212> TYPE: DNA
<213> ORGANISM: Artificial Sequence
<220> FEATURE:
<223> OTHER INFORMATION: primer F

<400> SEQUENCE: 19
tggacaagac caagaatgac attg                                            24

<210> SEQ ID NO 20
<211> LENGTH: 26
<212> TYPE: DNA
<213> ORGANISM: Artificial Sequence
<220> FEATURE:
<223> OTHER INFORMATION: primer

<400> SEQUENCE: 20
gttacaaata aagcaatagc atcaca                                          26

<210> SEQ ID NO 21
<211> LENGTH: 24
<212> TYPE: DNA
<213> ORGANISM: Artificial Sequence
<220> FEATURE:
<223> OTHER INFORMATION: primer

<400> SEQUENCE: 21
cagggttatt gtctcatgag cgga                                            24

<210> SEQ ID NO 22
<211> LENGTH: 22
<212> TYPE: DNA
<213> ORGANISM: Artificial Sequence
<220> FEATURE:
<223> OTHER INFORMATION: primer

<400> SEQUENCE: 22
```
gccacgccca ggaagagcat ga                                             22

<210> SEQ ID NO 23
<211> LENGTH: 22
<212> TYPE: DNA
<213> ORGANISM: Artificial Sequence
<220> FEATURE:
<223> OTHER INFORMATION: primer

<400> SEQUENCE: 23
gggccctctg gaaatgggga ga                                             22

<210> SEQ ID NO 24
<211> LENGTH: 24
<212> TYPE: DNA
<213> ORGANISM: Artificial Sequence
<220> FEATURE:
<223> OTHER INFORMATION: primer

<400> SEQUENCE: 24
caacccaggc ttgtcaccat cttt                                           24

<210> SEQ ID NO 25
<211> LENGTH: 22
<212> TYPE: DNA
<213> ORGANISM: Artificial Sequence
<220> FEATURE:
<223> OTHER INFORMATION: primer

<400> SEQUENCE: 25
gggtgaggtc gtggaccttg ga                                             22

<210> SEQ ID NO 26
<211> LENGTH: 28
<212> TYPE: DNA
<213> ORGANISM: Artificial Sequence
<220> FEATURE:
<223> OTHER INFORMATION: primer

<400> SEQUENCE: 26
cctaggaatt tcacaaataa agcatttt                                       28

<210> SEQ ID NO 27
<211> LENGTH: 23
<212> TYPE: DNA
<213> ORGANISM: Artificial Sequence
<220> FEATURE:
<223> OTHER INFORMATION: primer

<400> SEQUENCE: 27
cacccaactg atcttcagca tct                                            23

<210> SEQ ID NO 28
<211> LENGTH: 24
<212> TYPE: DNA
<213> ORGANISM: Artificial Sequence
<220> FEATURE:
<223> OTHER INFORMATION: primer

<400> SEQUENCE: 28
gcatggaagt gtcctttgag ttct                                           24

<210> SEQ ID NO 29
<211> LENGTH: 24
<212> TYPE: DNA

```
<213> ORGANISM: Artificial Sequence
<220> FEATURE:
<223> OTHER INFORMATION: primer

<400> SEQUENCE: 29
gacttgcaac gatgctcttt tgca                                          24

<210> SEQ ID NO 30
<211> LENGTH: 22
<212> TYPE: DNA
<213> ORGANISM: Artificial Sequence
<220> FEATURE:
<223> OTHER INFORMATION: primer

<400> SEQUENCE: 30
gagagagcat cgtcacaatg cc                                            22

<210> SEQ ID NO 31
<211> LENGTH: 21
<212> TYPE: DNA
<213> ORGANISM: Artificial Sequence
<220> FEATURE:
<223> OTHER INFORMATION: primer

<400> SEQUENCE: 31
gattccatcc agcaccgcac c                                             21

<210> SEQ ID NO 32
<211> LENGTH: 22
<212> TYPE: DNA
<213> ORGANISM: Artificial Sequence
<220> FEATURE:
<223> OTHER INFORMATION: primer

<400> SEQUENCE: 32
ctcagggtca atgccagcgc tt                                            22

<210> SEQ ID NO 33
<211> LENGTH: 23
<212> TYPE: DNA
<213> ORGANISM: Artificial Sequence
<220> FEATURE:
<223> OTHER INFORMATION: primer

<400> SEQUENCE: 33
gaataagggc gacacggaaa tgt                                           23

<210> SEQ ID NO 34
<211> LENGTH: 23
<212> TYPE: DNA
<213> ORGANISM: Artificial Sequence
<220> FEATURE:
<223> OTHER INFORMATION: primer

<400> SEQUENCE: 34
tgaagacagc ttgtcctgca caa                                           23

<210> SEQ ID NO 35
<211> LENGTH: 24
<212> TYPE: DNA
<213> ORGANISM: Artificial Sequence
<220> FEATURE:
<223> OTHER INFORMATION: primer

<400> SEQUENCE: 35
gatcatggct tggaggacca ttat                                          24
```

```
<210> SEQ ID NO 36
<211> LENGTH: 22
<212> TYPE: DNA
<213> ORGANISM: Artificial Sequence
<220> FEATURE:
<223> OTHER INFORMATION: primer

<400> SEQUENCE: 36
gctactgcat agagcgtcca tg                                            22

<210> SEQ ID NO 37
<211> LENGTH: 25
<212> TYPE: DNA
<213> ORGANISM: Artificial Sequence
<220> FEATURE:
<223> OTHER INFORMATION: primer

<400> SEQUENCE: 37
tttaccaggt aaaaacagaa accac                                         25

<210> SEQ ID NO 38
<211> LENGTH: 22
<212> TYPE: DNA
<213> ORGANISM: Artificial Sequence
<220> FEATURE:
<223> OTHER INFORMATION: primer

<400> SEQUENCE: 38
ctcagggtca atgccagcgc tt                                            22

<210> SEQ ID NO 39
<211> LENGTH: 23
<212> TYPE: DNA
<213> ORGANISM: Artificial Sequence
<220> FEATURE:
<223> OTHER INFORMATION: primer

<400> SEQUENCE: 39
cacccaactg atcttcagca tct                                           23

<210> SEQ ID NO 40
<211> LENGTH: 23
<212> TYPE: DNA
<213> ORGANISM: Artificial Sequence
<220> FEATURE:
<223> OTHER INFORMATION: primer

<400> SEQUENCE: 40
catggaacca ttccctatgg act                                           23

<210> SEQ ID NO 41
<211> LENGTH: 23
<212> TYPE: DNA
<213> ORGANISM: Artificial Sequence
<220> FEATURE:
<223> OTHER INFORMATION: primer

<400> SEQUENCE: 41
actggattgt gaaccaagga gtg                                           23

<210> SEQ ID NO 42
<211> LENGTH: 25
<212> TYPE: DNA
<213> ORGANISM: Artificial Sequence
<220> FEATURE:
```

```
<223> OTHER INFORMATION: primer

<400> SEQUENCE: 42
gaagaatgat tctgtaagtg tccag                                          25

<210> SEQ ID NO 43
<211> LENGTH: 22
<212> TYPE: DNA
<213> ORGANISM: Artificial Sequence
<220> FEATURE:
<223> OTHER INFORMATION: primer

<400> SEQUENCE: 43
cgttgccatg ccaatcttag cg                                             22

<210> SEQ ID NO 44
<211> LENGTH: 22
<212> TYPE: DNA
<213> ORGANISM: Artificial Sequence
<220> FEATURE:
<223> OTHER INFORMATION: primer

<400> SEQUENCE: 44
aatataaccc cgagcggcga tg                                             22

<210> SEQ ID NO 45
<211> LENGTH: 23
<212> TYPE: DNA
<213> ORGANISM: Artificial Sequence
<220> FEATURE:
<223> OTHER INFORMATION: primer

<400> SEQUENCE: 45
atgtcaccaa acagggtgcc caa                                            23

<210> SEQ ID NO 46
<211> LENGTH: 22
<212> TYPE: DNA
<213> ORGANISM: Artificial Sequence
<220> FEATURE:
<223> OTHER INFORMATION: primer

<400> SEQUENCE: 46
ggtgcttgcg tccttccacc aa                                             22

<210> SEQ ID NO 47
<211> LENGTH: 25
<212> TYPE: DNA
<213> ORGANISM: Artificial Sequence
<220> FEATURE:
<223> OTHER INFORMATION: primer

<400> SEQUENCE: 47
caaatgagta tggaatgctg gaaaa                                          25

<210> SEQ ID NO 48
<211> LENGTH: 22
<212> TYPE: DNA
<213> ORGANISM: Artificial Sequence
<220> FEATURE:
<223> OTHER INFORMATION: primer

<400> SEQUENCE: 48
gcgccgtgct ccattgattc tg                                             22
```

```
<210> SEQ ID NO 49
<211> LENGTH: 22
<212> TYPE: DNA
<213> ORGANISM: Artificial Sequence
<220> FEATURE:
<223> OTHER INFORMATION: primer

<400> SEQUENCE: 49
ggctgtgggc acatttgtca cg                                              22

<210> SEQ ID NO 50
<211> LENGTH: 22
<212> TYPE: DNA
<213> ORGANISM: Artificial Sequence
<220> FEATURE:
<223> OTHER INFORMATION: primer

<400> SEQUENCE: 50
ctcagggtca atgccagcgc tt                                              22

<210> SEQ ID NO 51
<211> LENGTH: 23
<212> TYPE: DNA
<213> ORGANISM: Artificial Sequence
<220> FEATURE:
<223> OTHER INFORMATION: primer

<400> SEQUENCE: 51
cacccaactg atcttcagca tct                                             23

<210> SEQ ID NO 52
<211> LENGTH: 21
<212> TYPE: DNA
<213> ORGANISM: Artificial Sequence
<220> FEATURE:
<223> OTHER INFORMATION: primer

<400> SEQUENCE: 52
ctgctcgggt gacctgtcct a                                               21

<210> SEQ ID NO 53
<211> LENGTH: 26
<212> TYPE: DNA
<213> ORGANISM: Artificial Sequence
<220> FEATURE:
<223> OTHER INFORMATION: primer

<400> SEQUENCE: 53
tgagatgttt ttcctattca gcaact                                          26

<210> SEQ ID NO 54
<211> LENGTH: 25
<212> TYPE: DNA
<213> ORGANISM: Artificial Sequence
<220> FEATURE:
<223> OTHER INFORMATION: primer

<400> SEQUENCE: 54
aacaatgtgt tgacgaacag agtta                                           25

<210> SEQ ID NO 55
<211> LENGTH: 22
<212> TYPE: DNA
<213> ORGANISM: Artificial Sequence
<220> FEATURE:
<223> OTHER INFORMATION: primer
```

```
<400> SEQUENCE: 55
ctccctgctg gacttgatag ag                                          22

<210> SEQ ID NO 56
<211> LENGTH: 22
<212> TYPE: DNA
<213> ORGANISM: Artificial Sequence
<220> FEATURE:
<223> OTHER INFORMATION: primer

<400> SEQUENCE: 56
ctcagggtca atgccagcgc tt                                          22

<210> SEQ ID NO 57
<211> LENGTH: 23
<212> TYPE: DNA
<213> ORGANISM: Artificial Sequence
<220> FEATURE:
<223> OTHER INFORMATION: primer

<400> SEQUENCE: 57
cacccaactg atcttcagca tct                                         23

<210> SEQ ID NO 58
<211> LENGTH: 23
<212> TYPE: DNA
<213> ORGANISM: Artificial Sequence
<220> FEATURE:
<223> OTHER INFORMATION: primer

<400> SEQUENCE: 58
ccacacaaca tgcgtaccaa gca                                         23

<210> SEQ ID NO 59
<211> LENGTH: 20
<212> TYPE: DNA
<213> ORGANISM: Artificial Sequence
<220> FEATURE:
<223> OTHER INFORMATION: primer

<400> SEQUENCE: 59
caggcgctgg cgctccgaca                                             20

<210> SEQ ID NO 60
<211> LENGTH: 24
<212> TYPE: DNA
<213> ORGANISM: Artificial Sequence
<220> FEATURE:
<223> OTHER INFORMATION: primer

<400> SEQUENCE: 60
gtctatggtt atactctctg aaca                                        24

<210> SEQ ID NO 61
<211> LENGTH: 22
<212> TYPE: DNA
<213> ORGANISM: Artificial Sequence
<220> FEATURE:
<223> OTHER INFORMATION: primer

<400> SEQUENCE: 61
gacaggagga cacaagtcag at                                          22

<210> SEQ ID NO 62
<211> LENGTH: 22
```

```
<212> TYPE: DNA
<213> ORGANISM: Artificial Sequence
<220> FEATURE:
<223> OTHER INFORMATION: primer

<400> SEQUENCE: 62
ctcagggtca atgccagcgc tt                                              22

<210> SEQ ID NO 63
<211> LENGTH: 1302
<212> TYPE: DNA
<213> ORGANISM: Artificial Sequence
<220> FEATURE:
<223> OTHER INFORMATION: Re-encoded sequences

<400> SEQUENCE: 63
gatcctgatt ccactattct agatataggg tctgcgccag caaggagaat gatgtcggac      60
agaaaatacc attgtgtttg tccgatgcgc agtgcggaag accctgagag actagcaaat     120
tatgcgagaa agctagcctc cgccgcaggg aaagtactgg ataggaatat ctctgggaaa     180
attggagacc tacaagcagt gatggcagtc cctgacacgg agacgcccac cttctgtctc     240
cacactgacg tatcttgcag gcaaagagct gatgtcgcaa tctaccaaga tgtttatgca     300
gtgcatgcac ccacgtcgtt ataccaccaa gcgattaaag gtgtgcgagt agcgtactgg     360
gtagggttcg atactactcc gttcatgtat aatgccatgg cggggcata tccaagctac      420 tcgacaaatt gggccgatga gcaggtgtta aaagccaaga atattggtct ttgcagcacc     480
gatttgacgg aaggtagacg aggaaaatta tctattatga ggggtaaaaa acttaaaccg     540
tgtgatcgtg ttctctttag tgtaggttca acgttgtacc cggagtcccg caagctcctt     600
aagagttggc atctgccctc ggtgttccac ttaaaaggta agctctcatt tacatgtcgc     660
tgtgacaccg tagtctcgtg cgaaggttat gttgtcaaaa ggataacgat gagccctggc     720
ctatacggaa aaacaaccgg atacgcggtc acccaccacg cagatggttt tctaatgtgc     780
aagaccacag atacggtaga cggagagagg atgtccttt cggtatgtac ttacgtgccg      840
gcgaccattt gcgatcagat gaccggcata ttggctacag aggtcacgcc ggaggatgct     900
cagaagttac ttgtgggttt aaatcaaagg atcgttgtaa acgggagaac gcaacggaac     960
acgaatacaa tgaaaaatta cttactacca gtggtcgctc aagcattctc caagtgggca    1020
aaagagtgtc ggaaagatat ggaggacgaa aaattattag gcgtcaggga agaacactc     1080 acctgttgct gcctctgggc tttcaagaag caaaaaacac acacggttta caaaaggccc    1140
gacacacaat ccattcagaa agtacaggcc gaattcgatt ccttcgttgt gccgtcattg    1200
tggtcgtccg gtttaagcat cccccctcaga acaaggatta agtggcttct ctccaaggtt    1260
ccaaaaacag atctcatacc atactccggg gacgcccgag ag                        1302

<210> SEQ ID NO 64
<211> LENGTH: 1410
<212> TYPE: DNA
<213> ORGANISM: Artificial Sequence
<220> FEATURE:
<223> OTHER INFORMATION: Re-encoded sequences

<400> SEQUENCE: 64
gccgtggccg cctgcaatga gttcttggca aggaactatc caacagtgtc cagttaccaa      60
attactgacg aatatgatgc ttatctagat atggtagacg ggtcggaatc atgcttagat     120
cgagcgacat ttaatccgtc taagttgagg tcttatccga aacaacatgc ataccacgcg     180
```

```
cctagcataa gaagcgctgt accgagtcct ttccagaata ctctgcagaa cgttttagcc    240
gccgccacga aaaggaactg caatgttaca cagatgaggg aactcccaac attagactcc    300
gctgtattta acgtcgaatg tttcaagaag tttgcatgca atcaagagta ttgggaagaa    360
tttgccgcct cccctatcag aataaccaca gaaaatttag ccacttacgt cactaaatta    420
aaaggcccta aggccgccgc gctgtttgct aaaactcata atttgcttcc cctgcaggaa    480
gttcccatgg ataggtttac tgtcgatatg aaaagggatg taaaagtgac tccaggtacc    540
aaacatactg aagaaaggcc aaggtgcaa gtgatccaag cggcagagcc cttagcgaca    600
gcctacttat gtggaattca tagagaattg gtgagaagat taaacgcagt cctcttgcct    660
aacgtgcata ctctttttcga catgtccgct gaagacttcg atgccataat agcagctcat    720
tttaaacccg gagatactgt gttggaaacg gatattgcat cattcgacaa aagccaagat    780
gacagtttag cgttaacagc tttgatgttg ttggaagact taggggtcga tcactcctta    840
ctagacctaa tagaagctgc cttcggggag atatcatctt gccatctacc gacaggtacg    900
cgctttaaat ttggcgccat gatgaagagc ggcatgttct taacattatt cgtaaatacc    960
ttgttaaaca ttaccatcgc aagtcgagtg ctagaggacc gtttaactaa gagtgcgtgt   1020
gcggcattta taggtgacga taacataatc catggggttg tgagtgatga attaatggct   1080
gccaggtgtg ctacctggat gaacatggag gtgaaaataa tcgatgcagt ggtctccctg   1140
aaggccccat acttctgcgg gggttttatc ctccatgaca ctgttaccgg caccgcatgt   1200
agagtagctg acccgttaaa aaggttgttt aaactcggca agccgctagc ggctggggat   1260
gaacaggacg aggataggag gcgagcgtta gcagatgagg tgatcaggtg caacgaact   1320 ggattgatcg acgagctaga gaaagcggtt tactcaagat acgaggtgca ggggattagt   1380
gtggttgtga tgtcaatggc cactttcgcc                                    1410

<210> SEQ ID NO 65
<211> LENGTH: 1500
<212> TYPE: DNA
<213> ORGANISM: Artificial Sequence
<220> FEATURE:
<223> OTHER INFORMATION: Re-encoded sequences

<400> SEQUENCE: 65
gttacgtggg gaaataatga gccgtacaaa tattggccgc agttgtccac caacggtaca     60
gctcatggtc atccgcatga gattatactc tactattatg aactatatcc aacaatgact    120
gtcgttgtcg ttagtgtggc aacgttcata ctactttcga tggtaggtat ggctgcgggg    180
atgtgcatgt gcgcacgacg cagatgcata actccgtatg aattaactcc cggcgcaaca    240
gtacccttcc tactaagctt aatctgctgc atcaggacag caaaggcggc cacttaccag    300
gaggccgcga tttacctgtg gaatgaacaa caacctctgt tttggttgca agcattaatc    360
ccgctagcag ctctcatagt tctgtgtaac tgtctgaggt tactcccctg ctgctgcaaa    420
acgttggcat tcctagcagt gatgtccgtg ggtgcccaca ctgtgtcagc gtatgaacac    480
gtgactgtca ttccgaatac ggtcggggtg ccgtataaaa ccttggtgaa tagacccgga    540
tactctccca tggttctgga aatggagctg ttgagcgtaa ctctggagcc tactctctcg    600
ctggattaca tcacgtgcga gtataagacc gtgataccga gcccgtacgt gaagtgttgt    660
ggaactgcag agtgcaaaga taagaacttg cccgactact cttgtaaagt tttcacaggc    720
gtttacccct tcatgtgggg tggggcatac tgttttttgtg acgcagaaaa tacgcagttg    780
tcagaagctc atgtagagaa gagcgagagc tgtaaaacag agttcgcttc cgcatacaga    840
```

```
gcccatactg catccgcttc cgcaaagcta cgcgttctat atcaaggcaa taatattact      900
gtgaccgcct acgccaacgg agatcatgca gttactgtta agacgcaaa attcattgta      960
gggcctatga gcagcgcatg accccctttt gacaacaaga tagtggttta aaaggagac     1020
gtatacaata tggattatcc gcccttggt gctggcagac ctgggcaatt tggtgatatc     1080
cagtcacgca cccctgaaag taaggatgtt tacgctaata cacagctcgt tctccagagg    1140
ccggcagtag gcacggtaca tgtaccctac tcacaggccc cttctggttt taaatactgg    1200
ctgaaggaac gcggtgcgtc gcttcaacat accgccccat tcggctgtca aattgccaca    1260
aacccggtta gggcggtcaa ctgcgctgta ggaaacatgc ctattagtat cgatatcccg    1320
gaggcggcat tcaccagggt ggtcgacgcg cctagtttaa cggatatgtc gtgcgaagtc    1380
cctgcttgta ctcacagtag tgattttggt ggcgtagcaa tcataaagta cgctgcctcc    1440
aaaaaaggaa aatgtgcggt gcactcgatg acaaatgcag ttactattcg ggaagccgag    1500
```

<210> SEQ ID NO 66
<211> LENGTH: 1412
<212> TYPE: DNA
<213> ORGANISM: Artificial Sequence
<220> FEATURE:
<223> OTHER INFORMATION: re-encoded cassette

<400> SEQUENCE: 66

```
ccgcggcgag tttaattaac ggagttgtta agctcttatc atggccatgg aacgcgcggg      60
aggatgtcgt gcgaatggcc atgaccgata ctaccgcctt tgggcagcag cgagtattca     120
aagagaaggt agataccaag gcccaggagc cccagccagg gacgaaggtg atcatgaggg     180
ccgtcaatga ctggattctt gagcgacttg cccgaaagag taagcctcgg atgtgtagta     240
gggaggaatt catagcgaag gtgaagagta acgcggctct tggggcctgg agcgatgagc     300
aaaatagatg gtcatccgct aaagaggccg tcgaggaccc cgcattttgg caactggtgg     360
acgaggaaag ggaaagacat ctggctggaa ggtgcgcaca ttgtgtctat aacatgatgg     420
ggaaaaggga gaaaaagctt ggagagtttg gtgttgctaa ggggagtcgg gccatttggt     480
acatgtggct gggcagccgc ttccttgagt tcgaagcact tggatttcta aacgaggacc     540
actgggcttc caggggggtcc agtggatcag gagttgaagg tatctcccta aattatttag     600
gatggtacct aaagggtttg agcactcttg agggcggact tttttacgca gatgacacag     660
ccggatggga taccaaggtc actaatgcag acttggagga tgaagagcag ctcctacgtt     720
acatggaggg tgaacacaag caactggcgg ctacaataat gcagaaggca taccacgcca    780
aagtggtaaa agttgcccgg ccctcccgag atggaggctg catcatggat gtcatcacta    840
gaagagacca aagaggctct ggccaagtag tgacttatgc cctaaacacc ctcaccaata    900
ttaaagtaca actgatacga atgatggaag gcgagggtgt catcgaagca acggacgccc    960
ataacccaag actgtttcga gtggaacgat ggctcaggga tcacggggag gaacgtcttg   1020
ggagaatgtt agtttccgga gatgactgtg tagtcagacc tgtcgatgac aggttcagta   1080
gagcgctata ttttctgaac gatatggcca aaacaagaaa ggatgtaggc gagtgggaac   1140
actcggtggg tttctcgaat tgggaggagg ttccttttg cagtcatcat tttcacgaat   1200
tagtgatgaa agatgggcgc gccttaatag tgccttgccg agaccaagat gaattggtgg   1260
gaagggcccg cgtctcccct gggtgcggct ggtcagttcg tgagacagcc tgtttgtcaa   1320
aggcatatgg ccaaatgtgg cttttatcct atttcatcg gcgcgatctc cgaacgttag   1380
```
gtttcgctat ctgttcggcg gtccccgtcg ac    1412

<210> SEQ ID NO 67
<211> LENGTH: 3569
<212> TYPE: DNA
<213> ORGANISM: Artificial Sequence
<220> FEATURE:
<223> OTHER INFORMATION: re-encoded cassette

<400> SEQUENCE: 67

```
ggagggaatg aaagctcgat aatgtggctt gcctcattgg caattgtaac agcttgtgca     60
ggagccatga aactatcaaa ctttcaagga aagttactga tgaccatcaa taacacggac    120
atagcggacg tcatcgttat ccccacctca aagggtgaaa acagatgctg ggtccgagca    180
atcgacgttg atacatgtg tgaagacaca atcacgtatg aatgtccgaa gcttgccgtg    240
ggcaatgatc cggaagacgt cgactgctgg tgcgacaatc aggaagtcta cgtgcaatat    300
ggacgctgca cacggaccag gcattccaaa cgatccagaa gatccgtttc ggtccaaacg    360
catgggaaa gttcactagt taacaaaaaa gaggcttggc tggactcaac gaaggcaacg    420
cgatacctca tgaaaacgga aaactggatc ataaggaacc caggttatgc cttcttggcg    480
gcggcacttg gatggatgct tggctcaaac agtggacaac gtgtggtgtt caccatcctc    540
ttattgttgg tcgctccggc ttacagcttc aactgtctgg gaatggggaa tcgggatttt    600
atagaaggag ccagtggagc cacttgggtg gatctggtgt tggaaggaga ttcctgtctt    660
acaatcatgg caaacgacaa gccaacacta gatgtccgca tgatcaacat tgaagccagc    720
caacttgctg aagtcagaag ttactgctat cacgcatcag tcaccgacat ttcaacggta    780
gctcgatgcc ccacgactgg agaagcccac aacgagaaac gtgcagatag cagctacgtg    840
tgcaaacaag gctttactga tcgcggatgg ggtaatggat gtggactttt tgggaaagga    900
agcattgaca catgcgcaaa atttagctgt accaataagg ccattggaag aatgatccaa    960
ccagagaata tcaagtacga ggttggcata ttcgtgcacg gaaccaccac ctcggaaaac   1020
catggaaatt attcagcgca gtaggagcg tctcaagcag caaagtttac tgtaacccca   1080
aacgctcctt caataaccct caagttaggt gattatggag aggtcacact ggactgtgaa   1140
ccaaggagcg gattaaatac tgaagcgttc tatgtgatga cagtgggctc gaagtcattc   1200
ctagtccaca gggaatggtt ccatgatctt tctcttccct ggacgagccc aagcagcacg   1260
gcatggagaa acagagaact cctcatggaa tttgaagagg cacatgccac aaaacaatct   1320
gtcgtagccc ttgggtcaca ggaaggtggc ctccatcaag cgctggctgg gccattgtg    1380
gtggagtact cgagctcagt gaagttgaca agtggacact gaaatgcag gctgaaaatg   1440
gacaaactgg ctttaaaggg cacgacttat ggcatgtgta cagaaaaatt ctcgttcgcg   1500
aaaaatccag cggacacagg ccatggaaca gtggtcattg agctaacata ttctggaagt   1560
gatggtccct gtaaaattcc gattgtctca gtggcgagtt aaacgacat gaccccagtg    1620
ggtaggctgg taacagtaaa ccccttcgtc gccacatcta gctccaactc aaaggttctg   1680
gttgagatgg aacctcccct cggagacagc tatatcgtgg tcggtagagg ggataagcag   1740
attaaccatc actggcacaa agctggaagc acgctgggca agctttctc aactaccttg   1800
aaagggctc agagattagc agcgctaggt gacactgcct gggacttcgg ctccattgga   1860
ggggtattta attctatagg gaaagctgtt caccaagtat tcggcggtgc tttcagaacg   1920
ctctttggtg aatgtcttg atcactcaa ggactaatgg ggggcctcct tttgtggatg   1980
ggtgttaacg cacgagatcg gtcaatagct ctggctttt tggccacggg aggtgtgctc   2040
```

-continued

```
gtcttttag cgaccaacgt gcatgccgac actggctgcg ccattgacat aactagaaaa    2100
gagatgagat gcggaagtgg catctttgtg cacaacgacg tagaggcttg ggtggatagg    2160
tacaaatatc tgccagagac gcctagatcc ctagcgaaga tagttcacaa ggcacatcaa    2220
gagggagtgt gcggggtcag atccgttact agactcgaac atcagatgtg ggaatctgtt    2280
cgggacgaat taaatgtctt gctcaaagag aacgcggtcg atttgagcgt ggtcgtgaac    2340
aaacccgtgg ggagatatcg ctcagctccc aaacgcctat ccatgactca agaaaagttc    2400
gagatgggct ggaaggcatg gggaaaaagc attctcttcg cccctgaatt ggccaactcc    2460
acattcgtcg tggatggacc cgagacaaag gaatgccctg atgagcgcag agcttggaac    2520
agcatgcaaa ttgaagattt cggattcggc ataacatcaa ctcgagtgtg gctgaaaatt    2580
agagaggaga acaccgatga gtgtgatgga gcaatcatag ggacagcagt aaagggacat    2640
gtggccgttc actccgactt gtcttactgg attgagagcc gtttgaatga cacctggaaa    2700
ttggagaggg ctgttttcgg agaggtaaaa tcttgcactt ggcccgaaac acacactctt    2760
tggggtgacg gagttgagga gagcgagctt atcatcccac atactatagc tggaccgaga    2820
agtaagcaca accggagaga agggtacaaa acacaaaacc agggaccctg ggatgagaac    2880
ggcatcgtgc ttgactttga ttattgtcca ggaacaaagg tcacaatcac agaggactgt    2940
ggcaaaaggg gtccctcaat cagaaccact actgacagtg aaagctgat caccgattgg    3000
tgctgtcgta gctgttctct accgccactc cggttccgga cagaaaatgg ttgctggtac    3060
gggatggaaa tcaggcctgt taggcatgac gaaacaacac tagttaggtc acaggttgac    3120
gctttcaacg gcgaaatgat tgacccattt cagctgggct tactggtgat gtttctcgca    3180
acccaggagg tccttcgcaa gaggtggacg gccagattaa cgattccagc ggttctaggg    3240
gctctacttg tgctgatgtt aggggcatc acttacactg acctgcaag atatgtcgtg    3300
ctagttgctg cggctttcgt ggaggccaac agtggtggag atgttctgca tctcgctctg    3360
atagccgttt tcaaaataca gccagctttt ctggttatga atatgcttag cgcgaggtgg    3420
acgaaccaag aaaacgtggt tctggtcctg ggggcggctt ttttccaact cgcttcagtg    3480
gatttacaga tcggagtcca cggaatcctc aatgccgctg ccatagcatg gatgatcgtt    3540
cgagcgatca catttcccac tacaagcac                                      3569
```

<210> SEQ ID NO 68
<211> LENGTH: 3569
<212> TYPE: DNA
<213> ORGANISM: Artificial Sequence
<220> FEATURE:
<223> OTHER INFORMATION: Re-encoded cassette

<400> SEQUENCE: 68

```
ggtgggaatg aaagctcgat aatgtggctg gcctcactcg ctattgtaac agcttgtgca      60
ggagcaatga aacttagcaa ttttcaggga aaattattaa tgacaatcaa taacacggac     120
atagcggacg tgatcgttat acccacaagc aagggagaaa acagatgctg ggtccgagct     180
atcgatgtcg gatacatgtg tgaagacaca atcacgtatg agtgtccgaa gcttgccgtg     240
gggaatgatc cggaagatgt cgactgttgg tgtgacaacc aggaagttta cgtccaatac     300
ggacgctgca cccggaccag gcacagcaaa cgatccagaa ggagtgtttc ggttcaaacg     360
catgggaga gttcactagt taataagaag gaagcctggc tggactcaac gaaggcaacg     420
cgataccctca tgaaaacgga aaactggata ataaggaacc caggatacgc cttcttggcg     480
```

```
gcggctcttg gatggatgtt agggtcaaac agtggacaac gtgtggtctt taccatcctc    540
ttattgcttg tagcaccggc ttacagcttc aactgcctgg ggatgggaaa tcgggatttt    600
attgaaggtg ccagtggtgc tacctgggtc gaccttgttc tcgaggggga ctcctgtctt    660
accatcatgg ctaacgacaa gcctacactt gatgtccgca tgattaacat tgaagcctct    720
caactagctg aagtgaggag ctattgctat catgcatcag ttaccgatat cagtacggta    780
gcacgatgcc ccacgacagg cgaagcccac aatgagaaac gtgcagatag ctcttacgtg    840
tgcaagcaag gttttacaga ccgcggatgg ggtaatggat gcgggttgtt tggcaaggga    900
agcattgaca cctgcgcaaa attcagctgc accaacaagg ccattggaag aatgatccag    960
cccgagaata tcaagtacga ggtaggaata ttcgtgcatg gcaccactac atcggaaaat   1020
catggaaatt atagcgcgca agtaggcgcg agtcaagcag caaaatttac cgtaaccccc   1080
aacgctccct caataacctt aaagttaggt gattatggtg aggtcactct agactgtgaa   1140
cccaggagcg gtttaaatac tgaggcgttc tatgtgatga cagttggctc gaagtctttc   1200
ctagtgcaca gggaatggtt tcatgattta agccttccct ggacgagccc aagcagcacg   1260
gcttggagaa acaggagct cctcatggag tttgaagagg ctcacgccac taaacaatct   1320
gtcgtggccc tagggagtca ggaaggtgga ctgcaccaag cgttggctgg ggccattgtt   1380
gttgaatact cgagcagtgt caaattgacc agtggacact tgaaatgcag gctgaaaatg   1440
gataaactgg ctttaaaagg cacgacatat ggcatgtgca cagaaaaatt ctcgtttgcg   1500
aagaaccccg cggacacagg acatggtact gtggttatcg agctaaccta ctcagggagt   1560
gacggtcctt gtaaaattcc gattgtttct gtggcgagct gaacgacat gaccccagtg    1620 ggtagactcg taacagtcaa cccattcgtc gccactagct caagtaactc caaagttctg   1680
gtcgagatgg aaccccatt tggagatagc tatatagtgg tgggtagggg ggataagcaa    1740
attaatcatc attggcacaa agccggatcc acgttgggca agctttctc aactaccttg    1800 aagggggctc agaggttagc agcgctaggt gacactgctt gggactttgg ctccattgga   1860
ggagtattta attctatagg gaaagcagtt caccaagtct ttggaggagc ttttaggacg   1920
ctctttggtg aatgtcatg gatcactcaa ggattgatgg gagcactcct gttgtggatg    1980
ggcgttaacg cccgagatcg gtctatagct ttagcatttt tggccacggg gggcgtgctc   2040
gtcttttggg cgactaacgt gcacgctgac actggctgcg caatagacat aactaggaaa   2100
gagatgagat gcggttccgg gatatttgtg cataacgacg tggaagcttg ggtggataga   2160
tacaaatatc tcccagaaac gcctagaagt ctggcgaaaa tagttcacaa ggcacatcaa   2220
gagggagttt gcgggggttag atctgttact aggctcgaac atcagatgtg ggaatctgtt   2280
cgggatgaat taaatgtctt gctaaaggag aacgcggtcg acttgagcgt ggtcgtgaac   2340
aaacctgtgg gaagatatcg cagtgctccc aaacgcctct ccatgacaca agaaaagttc   2400
gagatgggct ggaaggcatg gggcaaatcc atcttgtttg caccagaatt ggccaacagt   2460
accttcgttg tggatggacc cgagacaaaa gaatgccctg atgagcgcag agcttggaat   2520
tcaatgcaaa ttgaagattt tggattcggc ataacatcta ctcgagtttg ctgaaaatt   2580 agggaagaga acaccgacga gtgtgacggg gcaattatag gcacagcagt aaagggacac   2640
gtggccgttc actccgatct atcttactgg atcgaatctc gtttgaacga cacctggaag   2700
ttggagaggg ctgttttcgg ggaggtaaaa agttgcactt ggccagaaac acatacccctt   2760 tggggcgacg gagtagagga aagtgagttg ataatccccc atactatagc tggcccgaga    2820
agtaagcata accggagaga agggtacaaa actcagaatc agggaccatg ggacgagaac   2880
```

```
ggaatcgtgt tagactttga ttattgtccc ggaactaagg ttacaattac agaggattgt    2940
ggcaaaagag gtcctagcat cagaaccaca actgacagtg ggaagttaat aactgattgg    3000
tgttgtcgtt catgttccct gccgccactc cggttccgga cagaaaacgg ttgctggtac    3060
ggaatggaaa taaggcccgt tagacacgac gaaacaacac tagttaggtc acaggttgac    3120
gctttcaacg gcgagatgat tgacccattc caactgggct tactggtgat gttcctcgca    3180
actcaggagg tgttacgcaa gaggtggacg gctaggttaa cgattccagc ggttctaggc    3240
gcactgctcg tgctgatgtt agggggaata acctacactg acctggctag atatgtcgtg    3300
ctagttgctg cggccttcgt ggaggccaat agtggtggag atgttctgca tctcgccctg    3360
atcgcagttt tcaaaataca gccagcattc ctcgttatga atatgctttc agcgaggtgg    3420
acgaaccaag aaaatgtggt tctagtcctg ggagcggctt tcttccaact cgcatccgtg    3480
gacttacaaa ttggtgttca cggcatcctc aatgctgctg caattgcttg gatgatcgta    3540
cgagcgatca cttttcccac tacaagcac                                      3569
```

<210> SEQ ID NO 69
<211> LENGTH: 2853
<212> TYPE: DNA
<213> ORGANISM: Artificial Sequence
<220> FEATURE:
<223> OTHER INFORMATION: re-encoded cassette

<400> SEQUENCE: 69

```
ttgtcatagg aatttgttcc ctgctgcaag agaggagaaa gaccatggcg aagaagaaag      60
gagccgtgct cttgggctta gcgctcacat ctaccggatg gttctcgccc accactatcg     120
ctgccggact aatggtctgc aacccaaaca agaagagggg gtggccagcc accgaattcc     180
tttcagcggt tgggttgatg tttgccattg tgggaggcct agccgagttg gacatcgaat     240
ctatgtcaat acccttcatg ctggcagggc tcatggcagt atcctacgtg gtatcaggaa     300
aggcaaccga catgtggctg gatcgggctg ctgatatcag ctgggagatg gaggcagcta     360
tcacaggaag tagccggagg ctagatgtta agctggatga cgacggcgac tttcacttaa     420
ttgatgatcc cggagttcca tggaaagtct ggctcctccg catgtcttgt atcggattag     480
ccgctctgac accctgggct atcgtcccag ccgcttttgg ttattggctg acctgaaaa     540 caacaaaaag aggtggcgtg ttctgggaca cgccatctcc aaagccttgc ttaaaagggg     600
acaccaccac aggagtttac cgaattatgg ccagagggat tctcggcact taccaggccg     660
gtgtaggagt catgtacgag aacgttttcc atacattatg gcacacaact agaggcgcag     720
ccatcatgag cggagaagga aagctaacgc catactgggg tagtgtgaag gaagaccgca     780
taagctatgg aggcccgtgg aggttcgacc ggaaatggaa tggaacagat gatgtgcaag     840
ttatagtggt ggaaccaggg aaacctgcag taaacattca gacaaaaccg ggtgtgtttc     900 gcacccettt tgggggagatt ggagccgtca gcctggacta cccacggga acatccggct     960 ccccaatcct agattccaac ggagacatca taggcttgta cggcaatggg gttgagctcg    1020
gtgatgggtc gtatgtcagc gccattgtgc agggcgaccg tcaagaggaa ccagtccctg    1080
atgcctatac tccaagcatg ctaaaaaaga gacagatgac tgtgctggat ctgcacccag    1140
gttcggggaa aaccaggaag atccttcccc aaataataaa ggatgctata cagcagcgct    1200
tgagaacagc cgtgctggct ccaacacgag tcgtcgcagc tgagatggcg gaggccttga    1260
gaggtcttcc agtacgatat caaacctcag cagtgcagag ggagcatcag ggaaatgaaa    1320
```

```
ttgttgacgt aatgtgccat gccacactga ctcatagact aatgtctcca aacagggtgc    1380
ccaattacaa tttgttcgtt atggatgagg ctcacttcac tgatccagct agcatagccg    1440
ctcggggtta tatagcgacc aaggtggaac tgggggaggc agcagccatt tttatgacgg    1500 cgacccgcc cgggaccact gaccccttc ccgattcaaa tgctcccatt cacgacctgc    1560
aggatgagat cccagacaga gcatggagta gtggttacga atggatcacg gattacgcgg    1620
gaaaaactgt atggttcgtg gcaagtgtta aaatgggaaa cgagatcgcc atgtgcctcc    1680
aaagagcggg aaaaaaggtc atccaattga accgtaagtc atatgacaca gagtacccaa    1740
aatgtaagaa tggagactgg gactttgtga tcaccactga catctctgag atgggggcca    1800
attttggtgc gagcagggtt attgactgca gaaagtccgt gaaacctacc atcctagagg    1860
agggagaggg tagagtcatt ctcggaaacc catcccccat aaccagtgct agtgcagccc    1920
agcggagagg aagagtggga aggaatccca accaagttgg cgatgagtac cattatggag    1980
gggccaccag tgaagatgat agcaaccttg cccactggac agaggcaaaa attatgctag    2040
ataacataca catgcctaat ggcttagtgg ctcaactgta cgggcctgaa agggaaaagg    2100 cttttcacaat ggatgagaa taccgtttga gaggtgagga aagaagaac ttcttggagc    2160 tgcttagaac ggctgactta ccagtatggt tggcctacaa agtggcgtcc aatggcattc    2220
agtacacaga cagaaaatgg tgctttgatg gaccacgcac aaacgctata ctggaagata    2280
acactgaggt ggagatagtc acccgaatgg gtgagagaaa gatcctcaag ccagatggc    2340 tcgatgcgag ggtttatgca gaccaccaag ctctcaagtg gttcaaagat tttgcagcgg    2400
gcaagagatc tgccgtctcc ttcatagagg tactcggtcg catgccagag catttcatgg    2460
gaaagacacg ggaggcctta gacacaatgt acctcgtggc aacagccgag aaaggcggaa    2520
aggctcaccg catggctctt gaagaactgc ccgacgcatt ggagaccatc acactcatcg    2580
ttgccatcac tgtgatgaca ggaggatttt tcctgctcat gatgcaaaga aagggtattg    2640
gaaaaatggg cctaggggct ctagtgttga cgctggccac cttttttccta tgggcggctg    2700 aagtccctgg aactaaaatc gcgggcactc tactggttgc ccttttgctg atggtggtcc    2760
tcatcccgga accagaaaaa cagaggtcac agacagacaa tcagttggca gtatttctta    2820
tctgcgtcct gactgtggtc ggagtggtgg cag                                 2853

<210> SEQ ID NO 70
<211> LENGTH: 2853
<212> TYPE: DNA
<213> ORGANISM: Artificial Sequence
<220> FEATURE:
<223> OTHER INFORMATION: re-encoded cassette

<400> SEQUENCE: 70
ttgtcatagg aatttgttcc ctattgcaag aaaggagaaa aaccatggcg aagaaaaagg     60
gtgcagtgtt gcttggatta gcgctcacct ctactggctg gttctcgccc actaccatag    120
ctgccggtct aatggtatgc aatcctaaca aaaagagggg ttggcctgct accgaattcc    180
tgtctgcggt cgggttgatg ttcgccatag tgggcggcct agcagaactc gacatcgaat    240
caatgtctat tcccttatg ttggcaggc tcatggcagt aagctacgtc gtatcaggaa    300
aagctaccga catgtggctg atcgggctg ctgatatatc ttgggagatg gaggcagcta    360
tcacaggaag tagccggaga ttagatgtaa aactggatga tgacggcgac ttccacttaa    420
tagacgatcc cggagtgcca tggaaagtgt ggctcctccg catgagttgc ataggactgg    480
ccgctctgac tccttgggca atcgtcccag cagcctttg ttactggctg accttaaaaa    540
```

```
ccacaaaaag aggtggcgtg ttctgggata cgccatctcc caagccctgt ttaaaaggag      600
ataccaccac agggtctac  cgaattatgg ctagaggaat tcttggcact taccaggcag      660
gtgtaggagt aatgtacgaa aacgttttc  ataccttatg gcacactacc agaggcgcag      720
ccattatgag tggagaagga aagctcacgc cctactgggg tagtgtaaaa gaagaccgca      780
ttagctatgg aggtccgtgg aggtttgacc ggaaatggaa cggtacagat gatgtacaag      840
ttatagtggt ggaacccggg aaacctgcag taaacattca aactaaaccg ggtgtcttcc      900
gcactccatt tggggaaatt ggagccgtct ctctagatta tcctcggggg acaagcggct      960
ccccaatctt ggattccaac ggagatatta taggcttata cggtaatgga gtggagttgg     1020
gtgatgggtc gtatgtcagc gccatagtgc aaggcgatcg tcaagaggag ccagtccctg     1080
atgcttatac tccaagcatg ctaaagaaga gacagatgac tgtgctggat cttcaccctg     1140
gttcggggaa aactaggaag atacttcctc aaataataaa ggatgctata caacagcgct     1200
tgagaacagc agtcctggct ccaacacgag tcgtcgcagc tgagatggcg gaggccctga     1260
gaggtcttcc cgtacgatac cagacctctg cagtgcagag agaacatcag ggcaatgaaa     1320
ttgttgacgt aatgtgccac gctacactta ctcataggtt aatgtctcca aatagggtcc     1380
ccaattacaa tttgttcgtt atggacgagg ctcactttac cgatcccgct agcatagccg     1440
ctcggggtta catagcgacc aaggttgagc tcggagaggc agctgccatt tttatgacgg     1500
cgactccgcc aggaacaact gaccccttcc ccgatagtaa tgctcccatt cacgacctcc     1560
aggatgagat cccagacaga gcatggagta gtgttacga  atggatcacg gattacgcgg     1620
gaaaaactgt atggttcgtg gcttcagtta aaatgggaaa cgagatcgcc atgtgtctcc     1680
aaagagcggg aaaaaaagtc atccaattga accgtaagtc ctacgatact gagtacccca     1740
agtgtaagaa tggggactgg gactttgtga taacaacaga cataagtgag atgggcgcca     1800
acttcggcgc gagtagggtt attgattgta gaaagtccgt gaaacctacc atactggagg     1860
aaggcgaggg cagagtcatt ctcggcaacc cttccccaat aactagtgct agtgcagccc     1920
agcggagggg aagagtggga agaaatccca accaagttgg cgacgagtac cactatggag     1980
gggccactag tgaggatgat tcaaatcttg cccactggac tgaggctaaa attatgctgg     2040
ataatataca tatgcctaac ggccttgttg cacaactgta cgggcctgaa agggaaaagg     2100
cctttacaat ggacggagaa taccgtttga ggggtgagga gaaaaagaac ttccttgagc     2160
tgctgagaac ggctgactta cctgtttggt tggcctacaa ggtggcgtcc aatggcatcc     2220
agtacacaga tagaaagtgg tgttttgatg accacgcac  taacgctatc ctggaagata     2280
acaccgaggt agagatcgtg acccgaatgg gtgagaggaa gatcttaaag ccgagatggt     2340
tagacgcgag ggtttatgca gatcaccaag ccctaaaatg gttcaaagac ttcgcagcgg     2400
ggaagagatc tgccgtttcc ttcatagaag tattgggtcg catgccagag cacttcatgg     2460
gaaagacacg ggaggctttg gacaccatgt atctcgtagc aacagccgag aaaggcggaa     2520
aggctcatcg catggcactt gaagagctgc ctgatgcact ggaaactatc acactaatcg     2580
ttgcaatcac agtgatgaca gggggttttt tccttctgat gatgcaaaga aagggcattg     2640
gaaaaatggg ccttggagct ctagtgttga cgttagcaac tttttttcta tgggcggctg     2700
aagtccctgg aactaaaatc gcgggaactc tcctggttgc ccttctactg atggtcgtcc     2760
tcataccgga accagaaaaa cagagatctc agacagacaa tcagttggct gtattttaa     2820 tctgcgtctt aactgttgtt ggagtcgtcg cag                                  2853
```

<210> SEQ ID NO 71
<211> LENGTH: 3409
<212> TYPE: DNA
<213> ORGANISM: Artificial Sequence
<220> FEATURE:
<223> OTHER INFORMATION: re-encoded cassette

<400> SEQUENCE: 71

```
aggtctgacc ggattgccta gcatggctct ggacttgcgc ccagccacag cttgggcgct      60
gtatggggt agcacagttg tgttaacccc cctcctgaag cacctaatca cctcagaata     120
cgttaccaca tcgttagcat caataagttc ccaagcgggt tcgctgtttg ttttgccgcg     180
cggcgtgcct tttactgact tggatctaac cgttggactt gtctttctcg gctgctgggg     240
ccaaatcacc ctcaccacgt tcctaacagc tatggtacta gtaaccctcc actatggata     300
catgctgcct ggttggcaag cagaggcact aagagctgct cagagaagaa cagcggctgg     360
cataatgaag aatgcagttg tggacggaat ggtcgcaaca gacgtgcccg agcttgaaag     420
aactactccc ttgatgcaaa agaaagtcgg gcaagtgctc ttgataggg tgagcgtggc     480
ggcgttttg gtgaacccaa atgtcaccac cgtgagagag gcaggtgtat tggtgacggc     540
tgccacactc accttgtggg ataatggagc ctctgccgtc tggaacagca ccaccgccac     600
ggggctttgc catgtcatgc gaggcagcta tctagccggc ggatccatcg cctggactct     660
cattaaaaac gctgataagc cctccttaaa aaggggagg cctggtggca ggacgctagg     720
ggagcagtgg aaggagaaac ttaacgctat gagcagggat gagttcttca aatacagaag     780
agaggcaata attgaggtgg accgcactga agcacgcagg gctaggcgcg agaacaacat     840
agtgggagga catccagtct cgcgagggtc cgcaaagctc cgctggctcg tggaaaaagg     900
atttgtcagt ccaataggaa aggtcataga tctggggtgc gggcgcggag gctggagcta     960
ctacgcagca actctgaaga aagttcaaga agtcaaagga tacacgaaag gtggagcggg    1020
acacgaagaa ccgatgctca tgcaaagtta cggttggaac ctggtctcgt aaagagtgg    1080
ggtggacgta ttctacaaac cttcggagcc ttccgacacc ctgttctgtg acataggaga    1140
atctagccca gtccagagg tggaggagca acgcacgctg cgcgtcctag aaatgacatc    1200
cgactggcta atcggggcc ctagagagtt ttgcataaaa gttctctgcc cttacatgcc    1260
taaagttata gagaaaatgg aagtgttaca acgtcgtttc ggtggcggcc tggtgcgcct    1320
tccactttct cgaaactcta accatgagat gtattgggtg agtggagctg ccggcaatgt    1380
tgtgcatgcg gtcaacatga ccagccaagt gttactagga cgaatggatc gcacagtgtg    1440
gagaggtcca aagtatgaag aggatgtcaa tctgggcagc gggacgagag ctgtggggaa    1500
gggggaggtc catagcaacc aggaaaaaat taggaagaga atccagaaac tcagagaaga    1560
attcgcaaca acctggcaca aggaccctga gcacccatac cgaacctgga cctatcacgg    1620
aagctacgaa gtgaaggcta ctggcagcgc aagctctcta gtcaacgggg tggtaaaact    1680
catgtctaaa ccctgggatg ctatcgcaaa tgtcaccaca atggccatga cagacacaac    1740
cccctttggc cagcagaggg tcttcaagga aaggttgac acgaaggctc cagagccacc    1800
agcaggagtt aaagaagtgc taacgacac caccactgg ctgtgggccc atttgtcacg    1860
ggagaaacga cctcgcttgt gcactaaaga agaattcata aagaaagtga attctaacgc    1920
agctttagga gcagtgttcg ccgaacagaa tcaatggagc acggcgcggg aagctgtggg    1980
tgaccccctg ttttgggaga tggtcaatga agagagagag aatcatttgc gaggcgagtg    2040
ccatacgtgc atctacaaca tgatgggaaa aagagagaaa aaacccggag agttcgggaa    2100
```

```
ggccaaaggg agtagggcta tttggttcat gtggctcgga gctcggtacc tagagttcga    2160
agccctagga tttttaaatg aagaccattg gctttctcga gagaattcag gaggcggggt    2220
agaaggttca ggtgtgcaaa agttgggtta cattctccgg gacatagccg ggaagcaagg    2280
cggtaaaatg tatgctgatg acacagccgg gtgggacacc agaatcacca gaaccgactt    2340
agaaaatgaa gccaaagtgc ttgagctttt ggatggtgaa caccgcatgc tcgcccgagc    2400
cataattgaa ctaacgtaca ggcacaaagt ggttaaagtt atgagacctg ccgcaggagg    2460
aaagacagtg atggacgtga tatcccgaga agaccaaagg gggagtgggc aggtggtgac    2520
ctacgctctc aacacattca cgaacattgc cgtccaactg gtccgcttga tggaggcaga    2580
gggggtcatt ggaccccaac acttggaaca gctgcccagg aaaaacaaaa tagcagtcag    2640
gacatggctc tttgagaatg gagaggagag agtgactaga atggcgatca gtggagacga    2700
ctgtgtcgtt aagccgctgg atgacagatt cgccacggct ctccatttcc tcaatgcaat    2760
gtcgaaagtt agaaaggata tccaggaatg gaagccttcg catggttggc acgactggca    2820
gcaggtcccc ttttgctcca atcatttcca ggaaattgtg atgaaagacg aaggagcat     2880 agtcgtgccg tgcagagggc aggatgagct gattggcagg gcgcgcatct ccccaggtgc    2940
tggatggaat gtgaaggaca cagcttgtct ggccaaagcg tatgcacaga tgtggctgct    3000
cttgtacttc catcggaggg acctacgcct catggcaaat gcaatttgca gtgcagttcc    3060
agtggactgg gtgcccaccg gcagaacatc ctggtcaata catagcaaag gagagtggat    3120
gaccactgaa gacatgctgc aagtatgaa cagggtatgg attgaggaga atgagtggat    3180
gatggataaa accccaatca catcctggac agacgttccg tacgtaggaa agcgcgagga    3240
catctggtgt ggcagtctca tcggaacgcg aagcagggca acatgggctg agaacatcca    3300
cgcggctata aaccaagtga gggccatcat tggaaaagag aattatgttg attacatgac    3360
ttccctcaaa agatatgagg atgtattgat ccaggaggac agggtcatt                3409

<210> SEQ ID NO 72
<211> LENGTH: 3409
<212> TYPE: DNA
<213> ORGANISM: Artificial Sequence
<220> FEATURE:
<223> OTHER INFORMATION: re-encoded cassette

<400> SEQUENCE: 72
tggtctaacc ggccttccaa gcatggctct agacttgcgc ccagcaaccg cttgggcgtt     60
gtacgggggt agcactgtcg tactcactcc cctcttaaag cacctaatca cctcagaata    120
cgttactact tcgttagcaa gcataagttc ccaggcgggc tcgctgttcg tactcccgcg    180
cggcgtgccc ttcactgact tggatctaac tgtcggacta gtctttctcg gatgctgggg    240
gcaaataacc ttgacaacgt tcctaacagc catggtactc gtaaccctcc attatgggta    300
tatgctgcca ggttggcaag cagaggctct aagagcagcc cagagaagaa cagcggctgg    360
tattatgaag aatgcagttg tggatggaat ggtcgcaaca gacgtgcccg agcttgaaag    420
aactacacca ttgatgcaaa aaaaggtggg gcaagtgcta ttgataggtg tgagcgtcgc    480
ggcgttcttg gtgaatccaa atgtgaccac cgtcagagaa gctggggtat tggttacggc    540
tgccactctt accctctggg ataatggggc atctgctgtc tggaacagca ccaccgccac    600
ggggctttgt catgtcatgc gaggctcata tttagccggc ggaagcatcg cctggactct    660
cattaaaaat gccgataaac catcattaaa gagggggagg cccggtggga gaacgttagg    720
```

```
ggagcagtgg aaggagaaac ttaacgctat gtcaagggac gagttcttca aatatagaag    780
agaagcaatc attgaagtgg accgcactga agcacgcaga gctaggcgcg aaaacaatat    840
agttggcgga catccagtgt cgcgagggtc cgcaaagctc cgctggctag ttgaaaaggg    900
ttttgttagt ccaataggga aggtgatcga tttgggttgc gggcgcggag gttggagcta    960
ctacgcagca actctgaaga aggttcaaga ggtaaaggga tacacgaagg gtggagcggg   1020
gcacgaggag ccgatgctca tgcaatctta tggatggaac ctagtatcgc ttaaaagtgg   1080
ggtagacgta ttctataagc cttcggagcc ttccgacacc ctgttttgtg acatcggaga   1140
atctagccct agtccagagg ttgaggagca acgcacgtta cgcgtcttag aaatgacatc   1200
cgactggcta catcggggcc caagagaatt ttgcatcaaa gttctgtgtc catacatgcc   1260
taaggttatt gagaaaatgg aagtgttaca acgtcgtttc ggtgggggcc tcgtgcgcct   1320
tccactttcc cgaaatagta accacgagat gtattgggtg agtggcgctg ccggcaatgt   1380
tgtgcatgcg gtcaatatga ccagccaggt attactgggt cgaatggatc gcacagtctg   1440
gagaggtcct aaatatgaag aggatgtaaa tctgggttct gggacgaggg ctgtagggaa   1500
gggggaggtc catagcaacc aggaaaaaat taggaagagg atccagaaac tcagagaaga   1560
attcgcaaca acatggcaca aggaccctga gcacccctat cgaacctgga cctatcacgg   1620
ctcatatgaa gtaaaggcta ctggaagcgc atccagccta gtaaacgggg tagtaaaact   1680
aatgtctaaa ccctgggatg ctattgcaaa cgtgaccacc atggcaatga cagacacaac   1740
ccctttcggc cagcagagag tattcaagga gaaggtcgac acgaaggctc ctgagccccc   1800
agcaggggtt aaagaagtac taaatgaaac caccaactgg ctgtgggccc atctcagccg   1860
ggagaaacga cctcgcctgt gcactaaaga agagttcatt aagaaagtga attctaacgc   1920
tgcattagga gccgtattcg ccgaacaaaa tcagtggagc acggcgcggg aagccgttgg   1980
tgaccccctg ttttgggaga tggtaaacga ggagagagag aatcatttgc gaggcgaatg   2040
tcatacgtgc atttacaaca tgatgggcaa gagagaaaaa aaacccggtg aattcgggaa   2100
agccaaaggt agtagggcaa tatggttcat gtggctcggc gctcggtacc tagaatttga   2160
agctttgggc ttttttaaatg aagaccactg gctttctcga gaaaattctg ggggcggtgt   2220
agaaggatca ggtgtgcaaa aattgggtta tatacttcgg gatatagccg ggaaacaggg   2280
cggaaaaatg tatgctgatg acacagcagg atgggacacc agaatcacca gaaccgactt   2340
agaaaacgaa gccaaagtgc ttgagctcct tgatggtgaa caccgcatgc tcgcccgagc   2400
tatcattgaa ctaacgtaca ggcataaagt ggttaaagtt atgagacccg ccgcaggcgg   2460
aaagacagtg atggatgtaa tatcccgaga ggaccaaagg gggagtgggc aggtggtgac   2520
atacgccctt aacactttca cgaacattgc cgttcaactg gtacgcctta tggaggcaga   2580
aggtgttata ggcccccaac acctcgaaca gctccccaga aaaacaaaa ttgcagtcag   2640 aacatggcta ttcgagaatg gagaggagag agttactaga atggcgatca gtggtgatga   2700
ctgtgtagtt aaaccgctgg acgacaggtt cgcaacggca ctccacttcc tcaatgccat   2760
gtcgaaagtt agaaaggata tccaggaatg gaaaccctcg catgggtggc acgattggca   2820
acaggtcccc ttctgttcca atcacttcca ggaaattgtg atgaaagacg gaggagtat    2880 tgtcgtgccg tgcaggggggc aggacgagct tattggaagg gcgcgcatct ccccaggtgc   2940
tggatggaat gtgaaagaca cagcatgcct ggccaaagcg tatgcacaaa tgtggctgct   3000
tttgtacttc catcggagag acctacgcct tatggcaaac gccatttgca gtgcagtacc   3060
tgtggactgg gtgcccaccg gtagaacttc ctggtcaata catagcaagg gcgaatggat   3120
```

```
gaccactgaa gatatgctgc aagtatggaa cagggtatgg atagaggaga atgagtggat    3180
gatggataag acaccaataa catcctggac agacgttccg tacgtaggaa agcgcgagga    3240
catctggtgt ggcagtctaa tcggaacgcg aagcagagcc acttgggcag agaatatcca    3300
tgcggctata aaccaagtta gagctattat agggaaagag aattatgtgg attatatgac    3360
ttcacttaaa agatatgagg atgtattgat ccaagaagac agagtcatt              3409
```

METHOD FOR RAPID GENERATION OF AN ATTENUATED RNA VIRUS

The present patent application is filed pursuant to 35 U.S.C. 371 as a U.S. National Phase application of International Patent Application No. PCT/EP2015/063815, which was filed Jun. 19, 2015, claiming the benefit of priority to European Patent Application No. 14305956.6 (EP), which was filed on Jun. 20, 2014. The content of each of the aforementioned patent applications incorporated herein by reference in its entirety.

FIELD OF THE INVENTION

The present invention relates to a method for rapid generation of attenuated RNA viruses that may be used as vaccines to protect against viral infections and diseases.

BACKGROUND OF THE INVENTION

Many emerging infectious diseases are caused by single strand RNA viruses. The major outbreaks of dengue fever, West Nile encephalitis, Chikungunya fever, and Rift Valley fever that have occurred in recent decades, each with a significant impact on human health, highlight the urgent need to understand the factors that allow these viruses to invade new territories or adapt to new host or vector species.

These events are often perceived as a warning signs for a potential pandemic. In the case of pandemic, understanding the factors that shape the adaptability of these rapidly evolving infectious agents and our ability to promptly develop a vaccine will be the critical steps for controlling the spread of the disease.

Indeed, to this date, vaccination still remains the best approach for reducing mortality and morbidity of humans caused by such viruses. In particular, live attenuated vaccines are highly successful due to stimulation of different arms of the host immune response. These live attenuated vaccines are natural virus variants derived by passaging virus in abnormal hosts. However, the preparation of a live attenuated vaccine suffers from many drawbacks, especially since its preparation relies on an empirical and time-consuming method. Therefore, it currently takes a long time to develop a useful vaccine that can be administered to humans.

There is thus an unmet need for an approach of generating attenuated viruses, that has no possibility of reversion and that provides a fast, efficient, cost-effective and safe method of manufacturing a vaccine candidate.

The present invention fulfills this need by providing a systematic approach for designing future vaccine candidates that have essentially no possibility of reversion. This method is broadly applicable to a wide range of viruses and provides an effective approach for producing a wide variety of anti-viral vaccines.

SUMMARY OF THE INVENTION

The present invention harnesses the power of mutagenesis to produce an attenuated RNA virus in a very short period, i.e. as soon as the complete sequence of the target virus is known and an infectious genome can be produced.

Because there are more codons than amino acids, the genetic code is necessarily redundant. Different codons that encode the same amino acid are known as synonymous codons. Changes in the DNA sequence of a protein between two synonymous codons are often assumed to have no effect and are thus called synonymous mutation. However, even though synonymous codons encode the same amino acids, the inventors have shown that synonymous substitution over large regions of the viral genome results in the effective attenuation of the virus (Nougairede et al, *Random Codon Re-encoding Induces Stable Reduction of Replicative Fitness of Chikungunya Virus in primate and Mosquito Cells*, PLOS Pathogens, 2013). More precisely, the inventors founded out that replacement of native nucleotide codons of the genome of an RNA virus with synonymous nucleotide codons decreases the replicative fitness of the virus, thereby attenuating said virus.

The inventors also developed a novel approach for generating RNA viruses which does not require cloning and propagation of a full-length cDNA into a bacteria. This technology is based on the observation that overlapping double-stranded DNA fragments, each covering a portion of the viral genome, spontaneously enable recombination and synthesis of a DNA copy of the complete viral genome after transfection.

By combining these two approaches, the inventors developed a method for directly generating an attenuated virus, which has several advantages for vaccine candidate development, including the possibility of obtaining vaccine candidate in a very short period, as soon as the complete sequence of the targeted pathogen is known and an infectious genome can be produced. The method of the invention is thus extremely helpful for generating, within days, a live attenuated vaccine directed against a novel pathogen for which no treatment or vaccine is available.

Consequently, in a first aspect, the invention relates to a method for generating an attenuated RNA virus comprising the following steps:

step I) reencoding the viral genome of an infectious RNA virus by randomly substituting a part of the nucleotide codons of the entire viral genome of said infectious RNA virus by another nucleotide codon encoding for the same amino acid, with the proviso that:
  i) the number and position of rare nucleotide codons present in said viral genome are not modified, said rare nucleotide codons being CGU, CGC, CGA, CGG, UCG, CCG, GCG and ACG; and
  ii) the regions of said viral genome which are involved with RNA secondary structure are not modified.

step II) generating an attenuated RNA virus by:
sub-step II.a) introduction of a promoter of DNA-dependent RNA polymerase in position 5' and optionally a terminator and a RNA polyadenylation sequence in position 3' of the re-encoded viral genome as obtained in step I);
sub-step II.b) amplification of the re-encoded viral genome as prepared in sub-step a) including said promoter and optionally said terminator and RNA polyadenylation sequence, in at least 2, preferably at least 3, 4, 5 or 6 overlapping cDNA fragments;
sub-step II.c) transfection of said cDNA fragments into a host cell,
sub-step II.d) incubation of said host cell of sub-step c); and
sub-step II.e) recovery of the infectious RNA virus from said incubated host cell.

In a second aspect, the invention pertain to a pharmaceutical composition comprising an attenuated RNA virus obtained according to the method disclosed herein.

In a third aspect, the invention relates to the use of the method disclosed herein for developing a live attenuated vaccine, or the use of the attenuated RNA virus obtained according to the method disclosed herein as a live attenuated vaccine.

In a fourth aspect, the invention relates to the overlapping cDNA fragments obtained as disclosed in the method of the invention, for use as a vaccine.

DETAILED DESCRIPTION OF THE INVENTION

In a first aspect, the invention relates to a method for generating an attenuated RNA virus comprising the following steps:

step I) re-encoding the viral genome of an infectious RNA virus by randomly substituting a part of the nucleotide codons of the entire viral genome of said infectious RNA virus by another nucleotide codon encoding for the same amino acid, with the proviso that:
  i) the number and position of rare nucleotide codons present in said viral genome are not modified, said rare nucleotide codons being CGU, CGC, CGA, CGG, UCG, CCG, GCG and ACG; and
  ii) the regions of said viral genome which are involved with RNA secondary structure are not modified.

step II) generating an attenuated RNA virus by:
sub-step II.a) introduction of a promoter of DNA-dependent RNA polymerase in position 5' and optionally a terminator and a RNA polyadenylation sequence in position 3' of the re-encoded viral genome as obtained in step I);
sub-step II.b) amplification of the re-encoded viral genome as prepared in sub-step a) including said promoter and optionally said terminator and RNA polyadenylation sequence, in at least 2, preferably at least 3, 4, 5 or 6 overlapping cDNA fragments;
sub-step II.c) transfection of said cDNA fragments into a host cell;
sub-step II.d) incubation of said host cell of sub-step c); and
sub-step II.e) recovery of the infectious RNA virus from said incubated host cell.

Based on their thorough researches, the inventors developed a highly promising strategy for directly generating an attenuated virus by large-scale re-encoding.

Accordingly, the invention provides an attenuated virus, which comprises a modified viral genome containing nucleotide substitutions engineered in multiple locations in the genome, wherein the substitutions introduce a plurality of synonymous codons into the genome. The term "attenuated virus", as used herein, refers to a virus with compromised virulence in the intended recipient, e.g. human or animal recipient. More specifically, an attenuated virus has a decreased or weakened ability to produce disease while retaining the ability to stimulate an immune response similar to the wild type virus.

This novel strategy represents a significantly improved route to vaccine development. Indeed, site-directed re-encoding, associated with no modification of amino acid sequences, alleviates the likelihood of novel phenotypic properties and thus provides benefits to the generic development of live attenuated vaccines, including reduced costs and single dose induction of long-term immunity.

Large Scale Re-Encoding Step

The method of the invention comprises a first step I) of mutagenesis, also referred to as "large scale re-encoding" in the following. As used herein, the expressions "re-encoding method" or "large scale re-encoding method" refer to a step of re-encoding the viral genome of an RNA virus, preferably a region of said viral genome, by randomly substituting a part of the nucleotide codons of the entire viral genome of said infectious RNA virus by another nucleotide codon encoding for the same amino acid, with the proviso that:
  i) the number and position of rare nucleotide codons present in said viral genome are not modified, said rare nucleotide codons being CGU, CGC, CGA, CGG, UCG, CCG, GCG and ACG; and
  ii) the regions of said viral genome which are involved with RNA secondary structure are not modified.

Preferably, step I) is a step of re-encoding the viral genome of an infectious RNA virus by randomly substituting about 1% to about 20%, preferably about 1% to about 17%, preferably about 1% to about 15%, preferably about 1 to about 10%, preferably about 3 to about 8%, preferably about 3% to about 5% of the nucleotide codons of the entire viral genome of said infectious RNA virus by another nucleotide codon encoding for the same amino acid, with the proviso that:
  i) the number and position of rare nucleotide codons present in said viral genome are not modified, said rare nucleotide codons being CGU, CGC, CGA, CGG, UCG, CCG, GCG and ACG; and
  ii) the regions of said viral genome which are involved with RNA secondary structure are not modified.

The re-encoding method thus modifies the nucleic acid composition of large coding regions of the viral genome of RNA virus without modifying the encoded proteins by introducing a large number of synonymous mutations.

The starting material of step I) is preferably an infectious RNA virus. Preferably, the genome of the virus is re-encoded so that about 1% to about 20% of the nucleotide codons are substituted by different nucleotide codons which encode the same amino acid. This is possible thanks to the codon usage bias.

As used herein, the expressions "synonymous nucleotide codons" or "synonymous codons" refer to two or more nucleotide codons encoding the same amino acid. Indeed, most amino acids are encoded by more than one codon. Synonymous codons are codons that encode the same amino acid.

As used herein, the expressions "synonymous mutation" or "synonymous substitution" refer to the substitution of a nucleotide codon by another nucleotide codon which encodes the same amino acid, i.e. a synonymous codon. The inventors have shown that synonymous substitutions reduce a virus's replicative fitness. In addition, the introduction of synonymous codons into a virus genome limits its ability to mutate or to use recombination to become virulent. It is noteworthy that for obtaining an attenuated RNA virus, which could still be used as a live attenuated vaccines, only 1% to 20%, preferably 1% to 10% of the nucleotide codons of the viral genome are randomly re-encoded. In the context of the invention, the synonymous mutations are introduced by site-directed mutagenesis. Preferably, said mutations are inserted by cassette mutagenesis.

Whereas most amino acids can be encoded by several different codons, not all codons are used equally frequently some codons are "rare" codons. As used herein, a "rare" codon is one of at least two synonymous codons encoding a particular amino acid that is present in an mRNA at a significantly lower frequency than the most frequently used codon for that amino acid. Typically, said rare codons are CGU, CGC, CGA, CGG, UCG, CCG, GCG and ACG.

The method designed by the inventors is based on the observation that said rare codons should remain unchanged for efficiently controlling viral attenuation.

In addition, the inventors came to the conclusion that the regions of the viral genome involved with RNA secondary structure shall not be modified for efficiently controlling viral attenuation. Consequently, said regions are to be not re-encoded.

As used herein, the expression "regions of the viral genome involved with RNA secondary structure" refers to conserved regions of the genome of the virus, which contain functionally active RNA structures, also known as "RNA secondary structure". Said RNA structures are proved to be important during the various stages of the viral life cycle. The person skilled in the art would easily determine the regions involved with significant RNA secondary structure, which are usually well conserved in evolutionary phylogeny.

Basically, the step I) of re-encoding the genome of an infectious RNA virus comprises the following step:

identifying codons in multiple locations within non-regulatory portions of the viral genome, which codons can be replaced by synonymous codons, said codons being not CGU, CGC, CGA, CGG, UCG, CCG, GCG and ACG;

selecting a synonymous codon to be substituted for about 1 to about 20% of the identified nucleotide codons; and substituting a synonymous codon for each of the identified codons, preferably on the basis of the table 1 under.

Preferably, step I) is performed by:

determining the amino acid sequence encoded by the entire viral genome of the infectious RNA virus, and determining each nucleotide codon encoding each amino acid; and substituting about 1% to about 20%, preferably about 1% to about 17%, preferably about 1% to about 15%, preferably about 1 to about 10%, preferably about 3 to about 8%, preferably about 3% to about 5% of the nucleotide codon of the viral genome encoding an amino acid of table 1, by a different nucleotide codon encoding the same amino acid as specified in table 1:

TABLE 1

Synonymous mutation according to the invention

| Amino acid | Nucleotide codon |
| --- | --- |
| Ala, A | GCU, GCC, GCA |
| Arg/R | AGA, AGG |
| Asn/N | AAU, AAC |
| Asp/D | GAU, GAC |
| Cys/C | UGU, UGC |
| Gln/Q | CAA, CAG |
| Glu/E | GAA, GAG |
| Gly/G | GGU, GGC, GGA |
| His/H | CAU, CAC |
| Ile/I | AUU, AUC, AUA |
| Leu/L | UUA, UUG, CUU, CUC, CUA, CUG |
| Lys/K | AAA, AAG |
| Phe/F | UUU, UUC |
| Pro/P | CCU, CCC, CCA |
| Ser/S | UCU, UCC, UCA, AGU, AGC |
| Thr/T | ACU, ACC, ACA |
| Tyr/Y | UAU, UAC |
| Val/V | GUU, GUC, GUA, GUG |

The attenuated viruses, obtained according to the invention, have the remarkable property to be not modified at the protein level. Indeed, said attenuated viruses correspond to viruses which were genetically modified through synonymous substitutions, at the nucleic level only.

Viral attenuation can be confirmed in ways that are well known to one of ordinary skill in the art. Non-limiting examples include plaque assays, growth measurements, and reduced morbidity or lethality in test animals.

More specifically, the inventors have shown that the large scale re-encoding has an impact on the replicative fitness of the target RNA virus, thereby attenuating said virus.

"Replicative fitness" is defined as an organism's replicative capacity/adaptability in a given environment. The replicative fitness of a virus, or an attenuated virus obtained according to the method disclosed herein, can be measured in cellulo, for example by means involving competitions between two or more viral strains in tissue culture. Typically, the replicative fitness can be determined once the virus is recovered, in various type of cells such as non-human primate cells, or mosquito cells in the case of arboviruses. Typically, the re-encoded virus to evaluate and a wild type virus are passaged in various type of cells, such as non-human primate cells (Vero), or mosquito (C6/36). The replicative kinetics of each passages virus is determined using known techniques such as analysis of the viral growth rate, based on the analysis of TCID50 values.

The inventors have shown that the random re-encoding step decreases the replicative fitness of the virus in both primate (and arthropod cells in the case of arboviruses). The diminution of replicative fitness correlated directly with the degree of re-encoding. These results corroborates that codon re-encoding profoundly reduces the infectious titer of released virus whilst the number of viral particles remains stable.

Preferably, the attenuated RNA virus that the method aims to generate (also referred to as "target virus" herein) is an attenuated version of a single stranded positive RNA virus. More preferably said virus is selected from the group consisting of flavivirus, alphavirus and enterovirus.

A non-limiting list of flaviviruses comprises Dengue virus (DENV), Yellow fever virus (YFV), St Louis encephalitis (SLEV), Japanese encephalitis viruses (JEV), Murray Valley encephalitis (MVEV), West Nile virus (WNV), Rocio (ROCV), Tick-borne encephalitis virus (TBEV), Omsk hemorrhagic fever (OMSKV), Kyasanr Forrest disease (KFDV), Powassan (POWV). Preferably, said flavivirus is selected from the group consisting of:

Japanese encephalitis viruses (JEV); such as a genotype I strain (JEV I) or the genotype III strain (JEV III), West Nile virus (WNV), such as a genotype 2 strain;

Dengue virus (DENV), such as a serotype 4 strain;

Yellow fever virus (YFV), such as a South American wild-type strain; and

Tick-borne encephalitis virus (TBEV), such as a Far-Eastern subtype strain.

More preferably, said flavivirus is Tick-borne encephalitis virus

A non-limiting list of alphaviruses comprises Chikungunya virus (CHIK), Easterm equine encephalitis (EEE), Western equine encephalitis virus, Venezuelan equine encephalitis virus (VEE), Mayaro virus (MAY), O'nyong'nyong virus (ONN), Sindbis virus, Semliki Forest virus, Barmah Forest virus, Ross River virus, Una virus, Tonate virus. Preferably, said alphavirus is Chikungunya virus.

A non-limiting list of enteroviruses comprises Coxsackie, Echovirus, Poliovirus, and Rhinovirus. Preferably, said enterovirus is Coxsackie, more preferably Coxsackie B virus.

In one preferred embodiment, the target virus is Chikungunya virus. In this specific embodiment, the re-encoding step is performed in three regions of the viral genome, namely:

the region encoding thee non-structural protein nsP1;
the region encoding the non-structural protein nsP4; and
the region overlapping the structural protein E2 and E1.

Typically, mutations are introduced thanks to cassette mutagenesis, also called "re-encoded cassettes". Typically, a re-encoded cassette of about 1300 pb to about 1500 pb is used for each region.

In this embodiment, the viral genome of Chikungunya is modified as follows:

the region encoding the non-structural protein nsP1, in position 242-1543 (nt) of the complete genome is mutated by a re-encoded cassette of 1302 nt, as depicted in SEQ ID No: 63;
the region encoding the non-structural protein nsP4, in position 6026-7435 (nt) of the complete genome is mutated by a re-encoded cassette of 1410 nt, as depicted in SEQ ID No: 64; and
the region overlapping the structural protein E2 and E1, in position 9526-11022 (nt) of the complete genome is mutated by a re-encoded cassette of 1500 nt, as depicted in SEQ ID No: 65.

Typically, each of the re-encoded cassettes introduces 200 to 400 synonymous mutations, preferably about 250 to about 320, preferably about 266 to about 320. Preferably, the re-encoded cassette as depicted in SEQ ID No: 63, SEQ ID No: 64 and SEQ ID No: 65 respectively introduce 264, 298 and 320 synonymous mutations.

In another embodiment, the target virus is Tick-borne encephalitis virus (TBEV). In this specific embodiment, the re-encoding step is performed in the NS5 genomic region of the virus, which encodes the non-structural protein NS5. Typically a re-encoded cassette of about 1400 pb is used. In this embodiment, the viral genome of TBEV is modified to introduce about 200 to about 350 synonymous mutations, preferably about 200 to about 300, preferably about 225 to about 300, preferably about 225 to about 275, preferably about 225.

Preferably, the viral genome of the Tick-borne encephalitis virus is mutated by a re-encoded cassette of 1412 nt, depicted in SEQ ID No: 66. Said re-encoded cassette introduces 273 mutations.

In yet another embodiment, the target virus is Japanese encephalitis virus (JEV), preferably a genotype 1 strain. In this specific embodiment, the re-encoding step is performed in a large region of the viral genome, typically in almost all the complete open reading frame (ORF), from the beginning of PrM to the end of NS5 genomic region.

Preferably, the viral genome of JEV is modified to introduce about 163 to about 658, preferably about 163 to about 658 mutations.

Preferably, the viral genome of the Japanese encephalitis virus is mutated by at least one re-encoded cassette selected from the group consisting of:

re-encoded cassette Ia, as depicted in SEQ ID No: 67;
re-encoded cassette Ib, as depicted in SEQ ID No: 68;
re-encoded cassette IIa, as depicted in SEQ ID No: 69;
re-encoded cassette IIb, as depicted in SEQ ID No: 70;
re-encoded cassette IIIa, as depicted in SEQ ID No: 71; and
re-encoded cassette IIIb, as depicted in SEQ ID No:72.

More preferably, the viral genome of the Japanese encephalitis virus is mutated by a combination of re-encoded cassettes as follows:

combination of re-encoded cassettes Ia et IIa; or
combination of re-encoded cassettes Ia et IIIa; or
combination of re-encoded cassettes IIa et IIIa.

Alternatively, said virus is a single-stranded negative strand RNA virus. More preferably, said virus is a paramyxovirus, an arenavirus, a filovirus, a rhabdovirus, a bunyavirus or an influenza virus.

Direct Generation of an Attenuated RNA Virus

The method of the invention comprises a second step II) of direct generation of an attenuated RNA virus.

The inventors developed a novel approach to directly generate an attenuated RNA virus, starting from the randomly re-encoded viral genome of said virus. The inventors evidenced that overlapping cDNA fragments, each covering a portion of the genome of a RNA virus, can give rise to a virus without the use of a full-length cDNA or a plasmid or a vector comprising such full-length cDNA. Consequently, the inventors put light that overlapping double-stranded DNA fragments, each covering a portion of the attenuated viral genome, spontaneously enable recombination and synthesis of a DNA copy of the complete viral genome in cellulo.

Said method is highly advantageous, especially since it exonerates from:

constructing a full-length cDNA, covering the entire re-encoded viral genome; and/or
the use of a plasmid or a vector comprising such full-length cDNA; and/or
the necessity of reconstructing the full-length cDNA or the entire attenuated viral genome before transfection into a host cell; and/or
modifying the attenuated viral genome such as incorporating not naturally occurring recombination or restricting enzyme sites; and/or
using of helper virus or other viral protein.

This specific step II) of the invention, also referred to as "Infectious Subgenomic Amplicons" or "ISA", is thus a very simple procedure able to expedite production of attenuated RNA viruses within days, with perfect control of the viral sequences and starting from an re-encoded viral genome.

The strategy relies on the production of several cDNA fragments, each covering a fragment of the re-encoded viral genome. The assembly of the construct is not made in vitro by Gibson assembly or circular polymerase extension cloning before the transfection but through a recombination process that directly takes place in cellulo.

As used herein, the expression "generation of attenuated RNA viruses" refers to the production of an RNA virus, in a genetically modified form, i.e. in a re-encoded form according to the method of the invention.

As used herein, the expression "not naturally occurring recombination site" refers to sequences allowing site-specific recombination that can be exemplified by the Cre-Lox or FLP-FRT recombination systems. Restriction enzyme site refers to sequences allowing site-specific cutting of double stranded DNA by restriction enzymes that can be exemplified by the NotI or AluI endonucleases.

The step II) of the method of the invention comprises a sub-step II.a) of introducing a promoter of DNA-dependent RNA polymerase in position 5' of the entire genome of a RNA virus. Optionally, said sub-step II.a) further comprises the introduction of a terminator and a RNA polyadenylation sequence in position 3' of the entire genome of a RNA virus.

It is noteworthy that when the target virus is a polyadenylated virus, such as flavivirus, sub-step II.a) is a step of introducing a promoter of DNA-dependent RNA polymerase in position 5' and a terminator and a RNA polyadenylation sequence in position 3' of the entire genome of a RNA virus.

By including, at the 5' terminus of the first cDNA fragment, a promoter of DNA-dependent RNA polymerase, and at the 3' terminus of the last cDNA fragment a ribozyme sequence and a signal sequence for RNA poly-adenylation, the cDNA fragment is transcribed as a full-length RNA attenuated genome with authentic 5' and 3' termini.

Preferably, said promoter of DNA-dependent RNA polymerase in position 5' is the human cytomegalovirus promoter (pCMV), as depicted in SEQ ID No 1. Preferably, said terminator and RNA polyadenylation sequence is respectively the hepatitis delta ribozyme and the simian virus 40 polyadenylation signal (HDR/SV40pA). The sequence of HDR/SV40pA is depicted in SEQ ID No: 2.

Consequently, sub-step a) provides for the complete re-encoded viral genome of the RNA virus, flanked respectively in 5' and 3' by the human cytomegalovirus promoter (pCMV) (SEQ ID No:1) and the hepatitis delta ribozyme followed by the simian virus 40 polyadenylation signal (HDR/SV40pA) (SEQ ID No:2)

The step II) of the method of the invention comprises a sub-step II.b) of amplification of the entire re-encoded viral genome in several overlapping cDNA fragments. In sub-step II.b), the entire viral genome corresponds to the entire viral genome as prepared in step a), i.e. which includes said promoter and optionally said terminator and RNA polyadenylation sequence.

As used herein, the expression "overlapping cDNA fragments", cDNA fragments", also designated as "amplicons" or "DNA subgenomic fragments" or "subgenomic amplicons" are double-stranded DNA fragments covering only a portion of the re-encoded viral genome of a RNA virus.

Such fragments correspond to "subgenomic fragments".

The inventors enlightened that, when such fragments are transfected within a cell, they surprisingly spontaneously recombine in cellulo to reconstitute the entire re-encoded viral genome. Said recombination occurs even if the viral genome is not genetically modified to incorporate additional and not naturally occurring recombination sites.

cDNA fragments according to the invention encompass:
DNA fragments obtained by amplification, for example by PCR; as well as
DNA fragments obtained de novo.

Preferably, said cDNA fragments are non-infectious.

As used herein, the expression "full-length cDNA", refers to a DNA which comprises the entire viral genome of a virus into a single piece, preferably the entire re-encoded viral genome.

As used herein, the expression "cDNA fragment covering a portion of the entire re-encoded viral genome", refers to a DNA fragment which comprises a portion of the entire re-encoded viral genome. Typically, the cDNA fragments according to the invention recombine spontaneously upon transfection in cells to constitute a DNA copy of the entire re-encoded viral genome, flanked at the 5' terminus by a promoter of DNA-dependent RNA polymerase, and at the 3' terminus by a termination sequence and a signal sequence for RNA poly-adenylation. This construct is transcribed as a full-length RNA re-encoded genome with authentic 5' and 3' termini by the cellular machinery. On the contrary, a "full-length cDNA covering the entire viral genome" is a single cDNA which encodes for the totality of the viral genome, preferably the totality of the re-encoded viral genome.

Preferably, step II.b) of the method of the invention allows the production of from 2 to 15 overlapping cDNA fragments, preferably of 3, 4, 5, or 6 overlapping cDNA fragments. Typically, said cDNA fragments are of about 2 kb to about 6 kb, preferably of about 4 kb and each cDNA fragment has about 70 to about 100 bp overlapping regions.

Preferably, said overlapping cDNA fragments of step II.b) are:
fragments of infectious clone not amplified by PCR;
fragments of infectious clone amplified by PCR;
fragments of non infectious clone not amplified by PCR;
fragments of non infectious clone amplified by PCR;
fragments synthesised de novo not amplified by PCR;
fragments synthesised de novo amplified by PCR; and
fragments obtained by reverse-transcription PCR from the viral genome.

The step II) of the method of the invention comprises a sub-step II.c) of transfection of said cDNA fragments into a host cell.

As used herein, the term "transfection" refers to the introduction of nucleic acids (either DNA or RNA) into eukaryotic or prokaryotic cells or organisms. A cell that has taken up the exogenous nucleic acid is referred to as a "host cell" or "transfected cell." Transfection may be accomplished by a variety of means known in the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

Preferably, the host cell of sub-step c) is a permissive cell, which enables the recovery of an infectious virus. Typically, permissive cells employed in the method of the present invention are cells which, upon transfection with the cDNA fragments, are capable of realising a complete replication cycle of the virus, including the production of viral particles. Preferably, said host cell is selected from the group consisting of SW13, BHK-21, HEK 293 and Vero cell lines.

In a preferred embodiment, sub-step II.c) is a step of direct transfection of the cDNA fragments obtained in sub-step II.b) as such, and sub-step II.c) occurs directly after sub-step II.b). In this specific embodiment, cDNA fragments as such are transfected into the host cells. Said fragments spontaneously recombine in cellulo into a DNA copy of the entire re-encoded viral genome flanked at the 5' terminus by a promoter of DNA-dependent RNA polymerase, and at the 3' terminus by a termination sequence and a signal sequence for RNA poly-adenylation. As previously mentioned, the method of the invention overcomes a technical prejudice since it exonerates from transfecting a full-length cDNA, covering the entire viral genome, as such. Besides, the method is free from using a plasmid or a vector comprising said full-length cDNA as such and/or the necessity of reconstructing the full cDNA or the entire viral genome before transfection into a host cell.

On the contrary, the method relies on the transfection of the overlapping cDNA fragments, each comprising a portion of the re-encoded viral genome. The transfection of overlapping double-stranded DNA fragments, covering the entire genome of an RNA virus, into permissive cells enables recombination and synthesis of a DNA copy of the complete viral genome in cellulo.

In an alternative embodiment, sub-step II.c) is a step of transfection of plasmids each comprising a cDNA fragment obtained in sub-step II.b), wherein each cDNA fragment is incorporated in individual and separate plasmids or vectors.

In this embodiment, each cDNA fragment is incorporated into individual and separate plasmids or vectors. Each plasmid or vector comprises a single fragment of cDNA. In this embodiment, the entire re-encoded viral genome is reconstituted after transfection.

In one embodiment, the method of the invention comprises a further step II.b') after sub-step b) and prior to sub-step c) of purification of the overlapping cDNA fragments. Said purification can be performed by any known techniques, preferably through a chromatography column.

The step II) of the method of the invention comprises a sub-step II.d) of incubation of the host cells, which preferably lasts from 3 to 9 days. During said incubation step, the transfected cDNA fragments spontaneously recombine in the host cells to constitute a DNA copy of the entire re-encoded viral genome, flanked at the 5' terminus by a promoter of DNA-dependent RNA polymerase, and at the 3' terminus by a termination sequence and a signal sequence for RNA poly-adenylation. This construct is transcribed as a full-length RNA genome with authentic 5' and 3' termini by the cellular machinery.

Consequently, the product rescued in sub-step II.d) is an attenuated RNA virus.

Pharmaceutical Composition

In a second aspect, the invention pertains to a pharmaceutical composition comprising an attenuated RNA virus obtained according to the method disclosed herein.

All the previously disclosed technical data are applicable here.

Said pharmaceutical compositions comprising attenuated virus are suitable for immunization.

Preferably, administration of such the pharmaceutical composition of the present invention may be by various parenteral routes such as subcutaneous, intravenous, intradermal, intramuscular, intraperitoneal, intranasal, oral or transdermal routes. Parenteral administration can be accomplished by bolus injection or by gradual perfusion over time.

Preparations for parenteral administration include sterile aqueous or non-aqueous solutions, suspensions, and/or emulsions, which may contain auxiliary agents or excipients known in the art. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents.

When a composition of the present invention is used for administration to an individual, it can further comprise salts, buffers, adjuvants, or other substances which are desirable for improving the efficacy of the composition. For vaccines, adjuvants, substances which can augment a specific immune response, can be used. Normally, the adjuvant and the composition are mixed prior to presentation to the immune system, or presented separately, but into the same site of the organism being immunized.

The administration of the composition may be for either a "prophylactic" or "therapeutic" purpose. When provided prophylactically, the compositions of the invention which are vaccines are provided before any symptom or clinical sign of a pathogen infection becomes manifest. The prophylactic administration of the composition serves to prevent or attenuate any subsequent infection. In this embodiment, the invention pertains in the pharmaceutical composition as disclosed herein for use for preventing an RNA virus infection in a subject.

When provided therapeutically, an attenuated viral vaccine is provided upon the detection of a symptom or clinical sign of actual infection. The therapeutic administration serves to attenuate any actual infection. In this embodiment, the invention relates to the pharmaceutical composition disclosed herein for use for treating an RNA virus infection in a subject.

Thus, an attenuated vaccine composition of the present invention may be provided either before the onset of infection (so as to prevent or attenuate an anticipated infection) or after the initiation of an actual infection.

Designing Future Vaccine Candidate

In a third aspect, the invention relates to the use of the method disclosed herein for developing a live attenuated vaccine, or the use of the attenuated RNA virus obtained according to the method disclosed herein as a live attenuated vaccines.

All the previously disclosed technical data are applicable here.

The large scale codon re-encoding step of the invention has been shown to be a powerful method of attenuation which has several advantages for vaccine development, including the possibility to obtain potential vaccine strains in a very short period as soon as the complete sequence of the targeted pathogen is known and an infectious genome can be produced. The method of the invention is thus extremely helpful for generating, within days, a live attenuated vaccine directed against a novel pathogen for which no treatment or vaccine is available.

In addition, the inventors have shown that the method of the invention is advantageous in several aspects when designing future vaccine candidates, namely:

(i) reversion to wild-type is intrinsically more difficult, given the high number of mutations produced;

(ii) since the reduction of replicative fitness decreases with the degree of re-encoding, the method opens the door to finely tuning fitness reduction through modulation of the length of re-encoded regions and the number of synonymous mutations introduced;

(iii) the use of a combination of several re-encoded regions located throughout the viral genome prevents complete phenotypic reversion due to recombination between WT and re-encoded viruses: large scale sequence modification renders recombination intrinsically more difficult, and in the case of recombination, the part of the genome representing the re-encoded strain would likely still carry some mutations associated with fitness reduction.

Use of cDNA Fragments

The inventors met the burden to apply the method of the invention directly in vivo. By doing so, the inventors develop a method for creating a live attenuated vaccine directly within the body of a patient in need thereof. Said method is based on the administration of the overlapping cDNA fragments obtained from an infectious RNA virus which was re-encoded, according to the method disclosed herein.

Therefore, in a fourth aspect, the invention also relates to cDNA fragments for use as a vaccine, preferably as a live attenuated vaccine, wherein said cDNA fragments are overlapping cDNA fragments obtained by:

introducing a promoter of DNA-dependent RNA polymerase in position 5' and optionally a terminator and a RNA polyadenylation sequence in position 3' of a re-encoded viral genome; and amplifying said re-encoded viral genome in at least 2, preferably at least 3, 4, 5 or 6 overlapping cDNA fragments;

wherein said re-encoded viral genome is obtained by re-encoding the viral genome of an infectious RNA virus by randomly substituting a part of the nucleotide codons of the entire viral genome of said infectious RNA virus by another nucleotide codon encoding for the same amino acid, with the proviso that:
  i) the number and position of rare nucleotide codons present in said viral genome are not modified, said rare nucleotide codons being CGU, CGC, CGA, CGG, UCG, CCG, GCG and ACG; and
  ii) the regions of said viral genome which are involved with RNA secondary structure are not modified.

All the previously disclosed technical data are applicable here.

The following examples are given for the purpose of illustrating various embodiments of the invention and are not meant to limit the present invention in any fashion.

FIGURES LEGENDS

Figure 1:
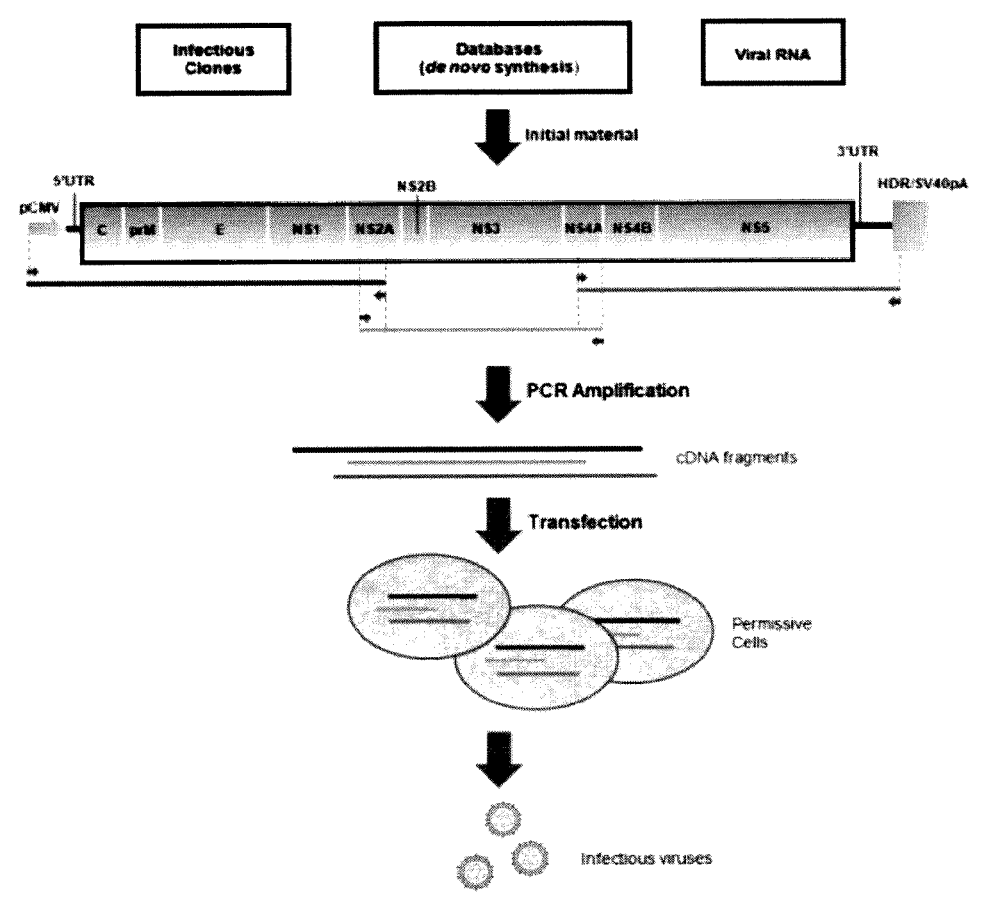

FIG. 1: Universal strategy to rescue single stranded positive RNA viruses.

The entire viral genome, schematically represented in the figure (flaviviral genome), flanked respectively in 5' and 3' by the human cytomegalovirus promoter (pCMV) and the hepatitis delta ribozyme followed by the simian virus 40 polyadenylation signal (HDR/SV40pA), was amplified by PCR in 3 overlapping cDNA fragments. Transfection of PCR products into permissive cells enabled the recovery of viruses after 3 to 9 days. Horizontal blue arrows represent primers used to generate the 3 overlapping cDNA fragments.

FIG. 2: Schematic representation of the CHIKV re-encoded viruses.

From top to bottom: Nucleotide scale bar; schematic representation of the CHIKV complete genome with coding regions (grey rectangles), non-coding (black rectangles) and the polyA tail. Re-encoded regions are represented in dark grey.

FIG. 3: Schematic representation of the 9 different re-encoded JEV obtained with the ISA method.

Each rectangle represents a fragment. Purple rectangles are used when no mutations were introduced (WT). Blue (low level of re-encoding) and green (high level of re-encoding) rectangles are used for re-encoded fragments (the value represents the number of synonymous mutations).

FIG. 4: Replicative fitness of the WT and re-encoded JEVs

In cellulo replicative fitness of re-encoded JEVs was measured using human cells .r Results show an decrease of the replicative fitness according to the level of re-encoding, the size of the re-encoding region and the genomic position of the re-encoded fragment(s).

EXAMPLES

Example 1: Generating an RNA Virus within Days

Example 1 illustrates the method ISA which allows the production of a RNA virus within days.

The following illustration of ISA is based on viral genomes which were not previously modified, i.e. viral genome which did not go through a re-encoding step.

Methods

Cells, Viruses, Infectious Clones and Antibodies

Baby hamster kidney (BHK-21) cells were grown at 37° C. with 5% CO2 in a minimal essential medium (Life Technologies) with 7% heat-inactivated foetal bovine serum (FBS; Life Technologies) and 1% Penicillin/Streptomycin (PS; 5000 U/mL and 5000 µg/ml; Life Technologies). Human embryonic kidney 293 (HEK-293) cells and African green monkey kidney (VeroE6) cells were grown at 37° C. with 5% CO2 in the same medium than BHK-21 cells supplemented with 1% of non-essential amino acids (Life technologies). Human adrenal carcinoma (SW13) cells were grown at 37° C. with 5% CO2 in RPMI 1640 medium (Life Technologies) with 10% FBS and 1% PS. JEV genotype I strain JEV_CNS769_Laos_2009 (KC196115) was isolated in June 2009 from the cerebrospinal fluid of a patient in Laos16; YFV strain BOL 88/1999 (KF907504), isolated in 2009 from a human serum, was kindly provided by the National Center of Tropical Diseases (CENETROP), Santa-Cruz, Bolivia; DENV-4 strain Dak HD 34 460 (KF907503), isolated from a human serum, was kindly provided by Robert B Tesh from the Center for Biodefense and Emerging Infectious Diseases—Sealy Center for Vaccine Development (University of Texas Medical Branch, Galveston, Tex., USA); the infectious clone of JEV genotype III derived from the strain rp9 (DQ648597) was kindly provided by Yi-Ling Lin from the Institute of Biomedical Sciences, Academia Sinica, Taipei, Taiwan; the infectious clone of WNV was derived from the strain Ouganda 1937 (M12294); the infectious clone of TBEV was derived from the strain Oshima 5.10 (AB062063); the infectious clone of CV-B3 was derived from the strain 2679 (KJ489414). A JEV-specific immune serum (obtain after vaccination against JEV) and monoclonal DENV-specific antibodies17 were used to perform direct immunofluorescence assays.

Preparation of cDNA Fragments

The complete genome flanked respectively in 5' and 3' by the human cytomegalovirus promoter (pCMV) (SEQ ID No:1) and the hepatitis delta ribozyme followed by the simian virus 40 polyadenylation signal (HDR/SV40pA) (SEQ ID No:2) was amplified by PCR in three overlapping DNA fragments of approximately 4.8 kb, 3.0 kb and 4.3 kb (4.8 kb, 2.9 kb and 5.2 kb for CHIKV, 4.8 kb, 4.1 kb and 3.4 kb for TBEV and 2.9 kb, 2.8 kb and 2.7 kb for CV-B3) (see Table 1 under).

For WNV, TBEV, JEV III and CHIKV, DNA fragments were obtained by PCR using infectious clones (for JEV III, a mutation was corrected using fusion PCR).

For JEV I (all DNA fragments), DENV-4 (first and third fragments) and YFV (first and third fragments), DNA fragments were synthesized de novo (Genscript) and amplified by PCR. Amplicons were produced using the Platinum PCR SuperMix High Fidelity kit (Life Technologies).

The mixture (final volume: 50 µL) consisted of 45 µL of supermix, 2 µL of DNA template at 1 ng/µL (infectious clone or synthesized DNA fragment) and 200 nM of each primer. For DENV-4 and YFV, the second DNA fragment was obtained by RT-PCR from clarified cell supernatants. Nucleic acids were extracted using the EZ1 Virus Mini Kit v2 on the EZ1 Biorobot (both from Qiagen) according to the manufacturer's instructions and amplified with the Superscript III One-Step RT-PCR Platinum Taq Hifi kit (Life Technologies). The mixture (final volume: 50 µL) contained 25 µL of Reaction Mix, 2 µL of nucleic acid extract, 100 nM of each primer, 1 μL of Enzyme Mix and 20 μL of Nuclease-Free Water. Assays were performed on a Biometra T-professional Standard Gradient thermocycler with the following conditions: 94° C. for 2 min followed by 40 cycles of 94° C. for 15 sec, 64° C. for 30 sec, 68° C. for 5 min and a preliminary step of 50° C. for 30 min for the RT-PCR. Size of the PCR products was verified by gel electrophoresis and purified using Amicon Ultra—0.5 mL kit (Millipore) according to the manufacturer's instructions. When plasmid DNA was used as template, the complete removal of the template was ensured by a digestion step with the restriction enzyme Dpn1 (New England Biolabs) before transfection. To control the efficiency of this additional step, the inventors transfected (see below), as a control, only two cDNA fragments (the first and the second, 1 μg final). These controls did not produce any infectious virus.

TABLE 2

Primers used to obtain cDNA fragments

| Virus | cDNA Fragment | Primer Forward | Position | SEQ ID | Primer Reverse | Position | SEQ ID |
|---|---|---|---|---|---|---|---|
| JEV I | I | CACCCAACTGATCTTCAGCATCT | — | 3 | GAAGAATGATTCTGTAAGTGTCCAG | 4054-4078 | 4 |
|  | II | CGTTGCCATGCCAATCTTAGCG | 4002-4023 | 5 | GGTGCTTGCGTCCTTCCACCAA | 6983-7004 | 6 |
|  | III | CAAATGAGTATGGAATGCTGGAAAA | 6932-6956 | 7 | CTCAGGGTCAATGCCAGCGCTT | — | 8 |
| JEV II | I | GCCCACCGGAAGGAGCTGAC | — | 9 | CAGAGAGCAAATCCCTATGACGA | 4078-4100 | 10 |
|  | II | CGTCACCATGCCAGTCTTAGCG | 4001-4022 | 11 | GCTTGGCAATCCAGTCAGTCCT | 7004-7025 | 12 |
|  | III | CAAACGAGTACGGAATGCTAGAAA | 6931-6954 | 13 | CTCATGTTTGACAGCTTATCATCG | — | 14 |
| WNV | I | TCAATATTGGCCATTAGCCATATTAT | — | 15 | TGGATTGAACACTCCTGTAGACGC | 4135-4158 | 16 |
|  | II | TGGTTGGAGTTGGAAGCCTCATC | 4052-4074 | 17 | GACCATGCCGTGGCCGCC | 7016-7034 | 18 |
|  | III | TGGACAAGACCAAGAATGACATTG | 6920-6943 | 19 | GTTACACAAATAAAGCAATAGCATCACA | — | 20 |
| TBEV | I | CAGGGTTATTGTCTCATGAGCGGA | — | 21 | GCCACGCCCAGGAAGAGAGCATGA | 4033-4054 | 22 |
|  | II | GGGCCCTCTGGAAATGGGGAGA | 3892-3913 | 23 | CAACCCAGGCTTGTCACCATCTTT | 8003-8026 | 24 |
|  | III | GGGTGAGGTCGTGGACCTTGGA | 7886-7907 | 25 | CCTAGGAATTTCACAAATAAAGCATTTT | — | 26 |
| YFV | I | CACCCAACTGATCTTCAGCATCT | — | 27 | GCATGGAAGTGTCTTTGAGTTCT | 4071-4094 | 28 |
|  | II | GACTTGCAACGATGTCTTTTGCA | 4020-4043 | 29 | GAGAGAGCATCGTCACAATGCC | 7040-7061 | 30 |
|  | III | GATTCCATCCAGCACCGCACC | 6964-6984 | 31 | CTCAGGGTCAATGCCAGCGCTT | — | 32 |
| DENV-4 | I | GAATAAGGGCGACACGGAAATGT | — | 33 | TGAAGACAGCTTGTCCTGCACAA | — | 34 |
|  | II | GATCATGGCTTGGAGGACCATTAT | 3980-4003 | 35 | GCTACTGCATAGAGCGTCCATG | 6949-6970 | 36 |
|  | III | TTTACCAGTAAAACAGAAACCAC | 6892-6916 | 37 | CTCAGGGTCAATGCCAGCGCTT | — | 38 |
| JEV I 6 fragments | I | CACCCAACTGATCTTCAGCATCT | 1560-1582 | 39 | CATGGAACCATTCCCTATGGACT | 1635-1657 | 40 |
|  | II | ACTGGATTGTGAACCAAGGAGTG | 4002-4023 | 41 | GAAGAATGATTCTGTAAGTGTCCAG | 4054-4078 | 42 |
|  | III | CGTTGCCATGCCAATCTTAGCG | 4002-4023 | 43 | AATATAACCCCGAGCGCGGATG | 5511-5532 | 44 |
|  | IV | ATGTCACCAAACAGGGTGCCCAA | 5440-5462 | 45 | GGTGCTTGCGTCCTTCCACCAA | 6983-7004 | 46 |
|  | V | CAAATGAGTATGGAATGCTGGAAAA | 6932-6956 | 47 | GCGCCGTGCTTGCTCCATTGATTCTG | 8950-8971 | 48 |
|  | VI | GGCTGTGGGCACATTTGTCACG | 8843-8864 | 49 | CTCAGGGTCAATGCCAGCGCTT | — | 50 |
| CHIKV | I | CACCCAACTGATCTTCAGCATCT | — | 51 | CTGCTCGGGTGACCTGTCTA | 4050-4070 | 52 |
|  | II | TGAGATGTTTTTCCTATTCAGCAACT | 3961-3986 | 53 | AACAATGTTGACGAACAGAGTTA | 6966-6990 | 54 |
|  | III | CTCCCTGCTGACTTGATAGAG | 6859-6880 | 55 | CTCAGGGTCAATGCCAGCGCTT | — | 56 |
| CV-B3 | I | CACCCAACTGATCTTCAGCATCT | — | 57 | CCCACACAACATGCTACCAAGCA | 2184-2206 | 58 |
|  | II | CAGCGGCTGCGCGTCCGACA | 2148-2167 | 59 | GTCTATGGTTATACTCTGAACA | 4970-4994 | 60 |
|  | III | GACAGGAGGACACAAGTCAGAT | 4921-4943 | 61 | CTCAGGGTCAATGCCAGCGCTT | — | 62 |

Cell Transfection

1 μg final of either an equimolar mix of all cDNA fragments amplified by PCR or 1 μg of infectious clone of CV-B3 was incubated with 12 μl of Lipofectamine 2000 (Life Technologies) in 600 μl of Opti-MEM medium (Life Technologies). According to the manufacturer's instructions, the mixture was added to a 12.5 cm2 culture flask of sub-confluent cells containing 1 mL of medium without antibiotics. After 4 hours of incubation, the cell supernatant was removed, cells were washed twice (HBSS; Life Technologies) and 3 mL of fresh medium was added. The cell supernatant was harvested when gross cytopathic effect (CPE) was observed (3-9 days depending on the cell type and the virus growth speed) or 9 days posttransfection for non cytopathic viruses, clarified by centrifugation, aliquoted and stored at −80° C. Each virus was then passaged four times using the same cell type except for the DENV-4 and YFV for which VeroE6 and HEK-293 were respectively used. Passages were performed by inoculating 333 μL of clarified cell supernatantonto cells in a 12.5 cm2 culture flask containing 666 μL of medium: after 2 hours of incubation, cells were washed twice (HBSS) and 3 mL of fresh medium was added. The cell supernatant was harvested after 2-6 days, clarified by centrifugation, aliquoted and stored at −80° C. Clarified cell supernatants (viruses stocks) were used to perform quantification of viral RNA, TCID50 assay, direct immunofluorescence assay and whole-genome sequencing.

Real Time PCR and RT PCR Assays

To assess the production of infectious viruses and ensure that positive detection was not the result of cDNA contamination, viral RNA was quantified and compared with the quantity of detected cDNA using the Access RT-PCR Core Reagent kit (Promega) with or without the reverse transcriptase. RNA was extracted using the EZ1 mini virus 2.0 kit and the EZ1 Biorobot (both from Qiagen) according to the manufacturer's instructions. The mixture (final volume: 25 μL) contained a standard quantity of AMV/Tfl 5× Reaction Buffer, 0.5 μM of each primer, 0.5 μL of dNTP Mix, 0.5 mM of MgSO4, 0.5 μL of AMV reverse transcriptase (only for RT-PCR), 0.5 μL of Tfl DNA polymerase, 15.5 μL of Nuclease-Free Water and 2 μL of extracted nucleic acids. Assays were performed using the CFX96 Touch™ Real-Time PCR Detection System (Biorad) with the following conditions: 50° C. for 15 min, 95° C. for 2 min, followed by 45 cycles of 95° C. for 15 sec, 60° C. for 40 sec. Data collection occurred during the 60° C. step. The difference between Cycle Threshold values (ct) obtained by Real time PCR and Real time RT-PCR assays has been used to assess viral RNA production. In addition, the amount of viral RNA expressed as dose detection limit (arbitrary unit; AU) was calculated from standard curves (nucleic acids from cell supernatants of cultured viruses were used as standard; five nucleic acid extracts were pooled and 10 μl-aliquots were stored at −80° C.).

Tissue Culture Infectious Dose 50 (TCID50) Assay

For each determination, a 96-well plate culture containing 20,000 BHK-21 cells in 100 μL of medium per well (added just before the inoculation) was inoculated with 50 μL of serial 10-fold dilutions of clarified cell culture supernatants: each row included 6 wells of the same dilution and two negative controls. The plates were incubated for 7 days and read for absence or presence of CPE in each well. The determination of the TCID50/mL was performed using the method of Reed and Muench[18].

Direct Immuno-Fluorescence Assay (dIFA)

Direct IFA were performed using 12.5 cm2 culture flasks of SW13 cells for JEV I and JEV III, and VeroE6 cells infected respectively 2 and 6 days before using clarified cell supernatant (see above: passage of viruses). The supernatant was removed and the cells washed twice (HBSS; Invitrogen), trypsinised, harvested and diluted (⅕) with fresh medium. After cytocentrifugation of 150 μL of this cell suspension (3 min, 900 rpm; Cytospin, Thermo Scientific), the slides were dried, plunged 20 min in cold acetone for fixation, dried, incubated 30 min at 37° C. with appropriately diluted JEV-specific immune serum (see above) or monoclonal DENV-specific antibodies, washed twice with PBS, washed once with distilled water, dried, incubated 30 min at 37° C. with the appropriately diluted FITC-conjugated secondary antibody and Evans blue counterstain, washed twice with PBS, washed once with distilled water, dried, mounted and read using a fluorescence microscope.

Sequence Analysis of the Full-Length Genome

Complete genome sequencing was performed using the Ion PGM Sequencer[19] (Life Technologies) and analyses conducted with the CLC Genomics Workbench 6 software.

Virus supernatants were first clarified and treated with the Benzonase nuclease HC >99% (Novagen) at 37° C. overnight. Following RNA extraction (no RNA carrier was used; see above) using the EZ1 mini virus 2.0 kit and the EZ1 Biorobot (both from Qiagen), random amplification of nucleic acids was performed as previously described [20]. Amplified DNA was analysed using the Ion PGM Sequencer according to the manufacturer's instructions. The read obtained were trimmed: first using quality score, then by removing the primers used during the random amplification and finally at the 5' and 3' extremities by removing systematically 6 nucleotides. Only reads with a length greater than 29 nucleotides are used and mapped to the original genome sequence used as a reference. Mutation frequencies (proportion of viral genomes with the mutation) for each position were calculated simply as the number of reads with a mutation compared to the reference divided by the total number of reads at that site.

Results

The inventors developed a simple and versatile reverse genetics that facilitates the recovery of infectious RNA viruses from genomic DNA material without requiring cloning, propagation of cDNA into bacteria or in vitro RNA transcription. Their working hypothesis was that transfection of overlapping double-stranded DNA fragments, covering the entire genome of an RNA virus, into susceptible cells would spontaneously enable recombination and synthesis of a DNA copy of the complete viral genome. By including at the 5' terminus of the first (5') DNA fragment, a promoter of DNA-dependent RNA polymerases, and at the 3' terminus of the last (3') DNA fragment a ribozyme sequence and a signal sequence for RNA poly-adenylation, the inventors anticipated that this genomic DNA copy would be transcribed as a full-length RNA genome with authentic 5' and 3' termini that would be efficiently exported out of the nucleus (in the case of a virus replicating in the cytoplasmic compartment).

The inventors first tested this hypothesis with 6 flaviviruses (i.e., arthropod-borne enveloped viruses with a single-stranded RNA genome of positive polarity that replicate in the cytoplasm of infected cells) that represent major flaviviral evolutionary lineages: two Japanese encephalitis viruses (JEV; genotype I (JEV I) and genotype III (JEV III)), one genotype 2 West Nile virus (WNV), one serotype 4 dengue virus (DENV-4), one wild-type strain of Yellow fever virus (YFV) and one Far-Eastern subtype Tick-borne encephalitis virus (TBEV) (Table 2).

Entire genomes were amplified by PCR in 3 DNA fragments of approximately 4 kb, each with 70-100 bp overlapping regions. The first and last fragments were flanked respectively in 5' and 3' by the human cytomegalovirus promoter (pCMV) and the hepatitis delta ribozyme followed by the simian virus 40 polyadenylation signal (HDR/SV40pA) (FIG. 1). PCR products were column-purified, and 1 μg of an equimolar mix of all fragments was transfected into SW13 and/or BHK-21 cell lines, which, ensure efficient recovery of flaviviral infectious genomes. Cell supernatant media from these infectious cultures were serially passaged four times using the same cell types, enabling the isolation of JEV I, JEV III, TBEV and WNV. For more demanding viruses, isolation could be achieved by passaging in additional permissive cells (e.g., DENV-4: VeroE6 cells; YFV: HEK-293 cells). Virus replication after four serial passages was demonstrated for each virus using a combination of the following criteria:
  (i) production of viral genomes in cell supernatant medium using real time RT-PCR methods,
  (ii) production of infectious particles in cell supernatant medium using TCID50 assays,
  (iii) detection of cytopathic effect (CPE),
  (iv) detection of viral antigens by direct immunofluorescence assays, and
  (v) complete viral genome sequencing using next generation sequencing (NGS) method.

The robustness, flexibility and versatility of the methods were further challenged as follows. Firstly, the inventors decreased the size and increased the number of overlapping fragments combined for transfection. This was exemplified in the case of JEV I, for which the ISA method generated infectious viruses, when using up to 6 overlapping amplicons of approximately 2 kb. Secondly, they applied the ISA method to viruses with a single-stranded RNA genome of positive polarity that belong to different families: Chikungunya virus (CHIKV, an enveloped virus, family Togaviridae) and Coxsackievirus B3 (CV-B3, a nonenveloped virus, family Picornaviridae). Again, infectious viruses could be isolated following transfection and four passages in HEK-293 cells (CHIKV) or BGM cells (CV-B3) (Table 2 under).

Furthermore, the inventors used as a control the CV-B3 obtained following transfection of a plasmid-bearing infectious genome and they obtained similar results in terms of infectivity and sequence data (Table 3).

TABLE 3

Characterization of the recovered viruses

| Virus | Strain | Origin of the material used to produce subgenomic amplicons | | | Cell line used for transfection | Cell line used during passages | Real time RT-PCR (U.A) | Log10 TCID50/ml |
|---|---|---|---|---|---|---|---|---|
| | | I | II | III | | | | |
| JEV | JEV I | DNS | DNS | DNS | BHK-21 | BHK-21 | 1.32E+08 | 5.8 |
| | | | | | SW13 | SW13 | 1.52E+07 | 5.2 |
| | | | | | SW13 * | SW13 * | 9.33E+06 | 2.8 * |
| | JEV III | I.C. | I.C. | I.C. | BHK-21 | BHK-21 | 3.77E+07 | 6.1 |
| | | | | | SW13 | SW13 | 4.04E+06 | 4.8 |
| | Chimeric JEV I/JEV III | DNS | I.C. | I.C. | BHK-21 | BHK-21 | 9.33E+07 | 6.7 |
| | | | | | SW13 | SW13 | 1.00E+07 | 6.8 |
| | Chimeric JEV III/JEV I | I.C. | DNS | DNS | BHK-21 | BHK-21 | 6.58E+07 | 6.6 |
| | | | | | SW13 | SW13 | 3.06E+07 | 6.4 |
| WNV | Ouganda | I.C. | I.C. | I.C. | BHK-21 | BHK-21 | 5.73E+07 | 5.3 |
| TBEV | Oshima 5.10 | I.C. | I.C. | I.C. | BHK-21 | BHK-21 | 3.28E+08 | 9.1 |
| DENV-4 | Dak HD 34 460 | DNS | Viral RNA | DNS | SW13 | VeroB6 | 6.59E+04 | N/A |
| YFV | BOL 88/1999 | DNS | Viral RNA | DNS | SW13 | HEK | 1.42E+05 | 5.2 |
| CHIKV | OPY1 | I.C. | I.C. | I.C. | HEK-293 | HEK-293 | 2.01E+07 | 7 |
| CV-B3 | 2679 | I.C. | I.C. | I.C. | SW13 | BGM | 4.64E+07 | 7.4 |
| CV-B3 ¶ | 2679 ¶ | Not obtained by PCR ¶ | | | SW13 ¶ | BGM ¶ | 9.33E+07 | 7.4 ¶ |

| Virus | Strain | CPE | dIFA | dN/dS (all mutations) | dN/dS (fixed mutations) | Substitutions per site after 4 passages (all mutations) | Substitutions per site after 4 passages (fixed mutations) |
|---|---|---|---|---|---|---|---|
| JEV | JEV I | Yes | N/A | 3.273 | N/A | 1.27E−03 | 7.29E−04 |
| | | Yes | Positive | 0.409 | N/A | 7.29E−04 | 9.11E−05 |
| | | Yes | N/A | N/A | N/A | N/A | N/A |
| | JEV III | Yes | N/A | 1.286 | 1.143 | 1.54E−03 | 1.45E−03 |
| | | Yes | Positive | 0.536 | N/A | 6.37E−04 | — |
| | Chimeric JEV I/JEV III | Yes | N/A | 0.404 | 1.571 | 1.36E−03 | 3.64E−04 |
| | | Yes | N/A | 1.19 | 1.589 | 9.10E−04 | 7.28E−04 |
| | Chimeric JEV III/JEV I | Yes | N/A | 0.268 | 0.268 | 2.73E−04 | 2.73E−04 |
| | | Yes | N/A | 5.357 | 3.178 | 1.00E−03 | 6.38E−04 |
| WNV | Ouganda | Yes | N/A | 0.268 | N/A | 4.55E−04 | 2.73E−04 |
| TBEV | Oshima 5.10 | Yes | N/A | 3.214 | N/A | 7.20E−04 | 9.00E−05 |
| DENV-4 | Dak HD 34 460 | No | Positive | 0.436 | 0.535 | 8.45E−04 | 5.63E−04 |
| YFV | BOL 88/1999 | Yes | N/A | 0.818 | 0.818 | 4.63E−04 | 4.63E−04 |
| CHIKV | OPY1 | Yes | N/A | 2.24 | N/A | 4.21E−04 | — |
| CV-B3 | 2679 | Yes | N/A | N/A | N/A | 2.70E−04 | — |
| CV-B3 ¶ | 2679 ¶ | Yes | N/A | N/A | N/A | — | — |

Thirdly, the inventors demonstrated the capability of ISA method to generate genetically modified viruses in days. This was exemplified by the PCR-based correction of a frame-shift mutation (1915del) in fragment one of a defective JEV III infectious clone and the subsequent recovery of the corresponding virus (Supplementary Methods). They were also able to produce chimeric viruses by exchanging the first DNA fragment (encoding structural proteins) of genotype I and III JEVs. Despite 11 mismatches in the overlapping region of the first two fragments, transfection resulted in the production of intergenotypic JEV I/JEV III and JEV III/JEV I chimeras. Analysis of complete genomic sequences established at the fourth passage, using NGS, showed that the genetic drift (rate of sequence change) was modest (ranging from 1.45E-03 to 9.00E-05 substitutions per site when considering fixed mutations). A majority of non-synonymous mutations, the presence of shared mutations amongst the different JEV strains (7/85), and the non-random distribution of mutations (at frequency above 10%) along the genome (with both hot spots and highly conserved regions) denoted adaptation to the cell culture conditions.

Summary of the different viruses produced in this study: the specific name of the strain, the origin of the initial material (DNS, De Novo Synthesis; I.C., Infectious Clone; or Viral RNA) used as the template for production of the first (I), second (II) and third (III) fragment, the cell line used for the transfection and the passages, the relative quantification of the amount of viral RNA and infectious titres in cell supernatants at the fourth passage by real time RT-PCR and TCID50 assay, the presence or absence of cytopathic effect (CPE) as well as the research of viral antigens by direct immunofluorescence assay (dIFA). Complete viral genome sequences were obtained using NGS technology.

dN and dS correspond respectively to the number of non-synonymous substitutions per non-synonymous site and the number of synonymous substitutions per synonymous site.

\* Results obtained by transfection of six overlapping fragments.

¶ Results obtained by transfecting directly the CV-B3 plasmid-bearing infectious clone.

N/A and AU mean not available and arbitrary unit respectively.

The mutation rate varied according to the cells used for isolation and, as expected, was higher in viruses derived from low-passage strains than in those derived from culture-adapted strains. In conclusion, the ISA method is a very simple procedure with which to expedite production of infectious genetically modified RNA viruses within days, with perfect control of the viral sequences and starting from a variety of initial sources including pre-existing infectious clones, viral RNA or de novo synthesized DNA genomic sequences. This technique has the future potential to generate the design of large reverse genetics experiments for RNA viruses, on a scale that could not previously have been considered. It also has the capacity, specifically to modulate the characteristics of the viruses recovered from experimental procedures. Additionally, because DNA subgenomic fragments can conveniently be obtained by PCR, this method has the potential to conserve the genetic diversity of viral populations13 when starting from viral RNA. Error-prone PCR may be also be used to create artificial viral heterogeneity, e.g. for facilitating the selection of adapted viruses15 under various experimental selection conditions and, conversely, high-fidelity polymerases and clonal amplification templates may be used to control the degree of clonality of the viruses produced.

Finally, the method of the invention has the potential to revolutionise the safety and security of future exchanges of RNA viruses between scientific institutions, by the separate shipment at room temperature of simple, on-infectious, DNA subgenomic fragments that, could then be combined and transfected by the recipient institute, enabling rapid, simple and safe recovery of the infectious viral strain.

Example 2: Attenuation of Chikungunya

Materials and Methods

Cells and Antibodies

African green monkey kidney (Vero) cells were grown at 37° C. with 5% $CO_2$ in a minimal essential medium (Invitrogen) with 7% heat-inactivated fetal bovine serum (FBS; Invitrogen) and 1% Penicillin/Streptomycin (PS; 5000 U/ml and 5000 µg/ml; Invitrogen). Human embryonic kidney 293 (HEK293) cells were grown at 37° C. with 5% $CO_2$ in Dulbecco's modified Eagles medium (Invitrogen) with 10% FBS and 1% PS. *A. albopictus* C6/36 cells were grown at 30° C. in L-15 medium (Invitrogen) with 10% heat-inactivated FBS, 1% PS and 5% tryptose phosphate broth (29.5 g/L; Sigma-Aldrich).

A CHIKV-specific immune human serum was used to perform the ELISA assay (see below). To decrease the concentration of non-specific molecules that react with HEK293 cell compounds, 40 µl of serum was put in contact 16 hours with extracted HEK293 cells (cells obtained from one 150 cm2 flask culture, extracted using acetone) in a final volume of 400 µl (diluents: 1% BSA; KPL). A recombinant protein (fusion between the C-terminal region of the nsP2 and the N-terminal region of the nsP3; Text S2), kindly provided by the AFMB laboratory (Architecture et Fonction des Macromolécules Biologiques, UMR 6098, Marseille France), was used to immunize two rabbits using standard methods (Rabbit Speedy 28-days immunization protocol, Eurogentec). Purified polyclonal antibodies (Affinity purification using a Sepharose matrix; Eurogentec) were used to perform the western blot analysis.

In Silico Re-Encoding Method

Three regions of the CHIKV genome were re-encoded using a computer program that randomly attributed nucleotide codons based on their corresponding amino acid sequence: for example, the amino acid valine was randomly replaced by GTT, GTC, GTA or GTG. To minimize the influence of rare codons in primate cell lines, the number and the position of such rare codons in primate genomes (i.e. CGU, CGC, CGA, CGG, UCG, CCG, GCG, ACG) were not modified. In addition, unique restriction sites were conserved by correcting synonymous mutations at some sites. The location of the re-encoded cassettes, first based on the availability of unique restriction sites was adjusted to avoid overlap with known RNA secondary structures. Finally, three cassettes of 1302, 1410 and 1500 bases and located in the nsP1, nsP4 and E2/E1 regions, respectively, were designed using this method (the sequences of the cassettes are respectively depicted in SEQ ID No: 63, SEQ ID No: 64 and SEQ ID No: 65).

Construction of CHIKV Infectious Clones (ICs)

We modified a previously described IC of the LR2006 strain (GenBank accession EU224268) by replacing the origin of replication and the prokaryote promoter by a modified pBR322 origin and a promoter CMV (pCMV), respectively. BamHI and XhoI unique restriction sites were used to obtain an intermediate plasmid using standard molecular techniques which contained a new origin of replication (modified pBR322), the prokaryote promoter CMV (pCMV) and the partial viral genome (from the first base to XhoI). The partial viral genome (from XhoI to the end), the polyA tail and the hepatitis D ribozyme (HDR) followed by a Simian virus 40 (SV40) polyadenylation was synthesized (Genscript) and introduced into the intermediate construct using XhoI and AvrII unique restriction sites. Finally, unique restriction sites BamHI, AgeI and XhoI were used to introduce synonymous mutations into the genome (mutated cassettes were obtained by fusion of PCR products). A total of eight synonymous mutations were introduced to generate the required restriction sites or to eliminate undesirable restriction sites. The infectious clone obtained, which was considered the wild-type (WT), incorporated four new unique restriction sites.

All the re-encoded regions were synthesized (GenScript) and then inserted into ICs by digestion (BamHI/XmaI for Φnsp1, AgeI/ApaI for Φnsp4 and XhoI/AvrII for Φenv; NewEngland Biolabs), gel purification of digestion products (Qiagen), ligation (T4 DNA ligase; Invitrogen) and transformation into electrocompetent STBL4 cells (Invitrogen). Before their transfection, all the infectious clones were purified (0.22 μm filtration) and their integrity was verified by restriction map and complete sequencing using a set of specific primer pairs.

Real Time RT-PCR Assays

A fragment of 179 nt located in the nsP2 region (nucleotide position 2631 to 2809) was used to detect the genomic RNA (plus strand) of all the CHIKVs (universal assay), re-encoded or not. Another fragment of 168 nt located in the nsP4 region (nucleotide position 6804 to 6971) was used to analyze cell supernatants from competition experiments: two sets of primers and probes allowed us to specifically detect either the viruses re-encoded in the nsP4 region or the viruses without modification in the same region.

Replication Kinetics

The replicative fitness of each virus was determined using the results of replication kinetics studies, performed in triplicate in Vero, HEK293 or C6/36 cells. For comparison of the seven viruses from the seven ICs (the WT virus and the 6 re-encoded viruses), one experiment was performed with all the viruses. Virus stock or ICs were used to infect or transfect cells respectively. For the evaluation of replicative fitness of the passaged viruses, the inventors performed one experiment for each virus (WT, Φnsp4 and Φnsp1 Φnsp4 Φenv viruses) with the first passage in Vero and the 12th, 25th, 37th and 50th passages for each passage regimen (13 supernatants tested in triplicate). For the single cycle replication kinetics, an estimated MOI of 5 was used to infect a 75 cm2 culture flask of confluent Vero, C6/36 or HEK293 cells. Cells were washed twice (HBSS) 30 minutes after the infection and 20 ml of medium was added. 1 ml of cell supernatant was sampled just before the washes and at 2, 8, 14, 20 and 28 hours pi. For the replication kinetics with low estimated MOI and the evaluation of the replicative fitness of the passaged viruses, an estimated MOI of 0.01 was used to infect a 25 cm2 culture flask of confluent Vero or C6/36 cells. Cells were washed twice (HBSS) 2 hours after infection and 8 ml of medium was added. 1 ml of cell supernatant was sampled after the washes (TO) and at 24, 48 and 72 hours pi. For the replication kinetics using infectious DNA clones, a 75 cm2 culture flask of subconfluent HEK293 cells was transfected with the ICs using Lipofectamine 2000 (Invitrogen) according to the manufacturer's instructions. Cells were washed twice (HBSS) 4 hours after the transfection and 20 ml of medium was added. 1 ml of cell supernatant was sampled after the washes (TO) and at 16, 24 and 48 hours pi.

All the sampled cell supernatants were clarified by centrifugation, aliquoted and stored at −80° C. They were then analysed using a TCID50 assay and a real time RT-PCR assay (not performed systematically, see figure legends). Nucleic acids were extracted from clarified cell supernatants using the EZ1 Virus Mini Kit v2 on the EZ1 Biorobot (both from Qiagen).

Virus Competition Experiments

WT virus was grown in competition with one of four re-encoded viruses Φnsp4, Φnsp1 Φnsp4, Φnsp1 Φenv or Φnsp1 Φnsp4 Φenv) using five different PFU ratios (WT/re-encoded virus 1/99, 20/80, 50/50, 80/20, 99/1). A global estimated MOI of 0.5 was used for the first inoculation. For each experiment, a 25 cm2 flask culture of confluent cells was infected for 2 hours, washed (HBSS) and then incubated for 48 h after the addition of 7 ml of medium. Viruses from each experiment were then passaged nine times as follows: a 25 cm2 flask culture of confluent cells was infected for 2 hours with the purified culture supernatant (centrifugation), washed (HBSS) and then incubated for 48 h after the addition of 7 ml of medium. At each passage, the estimated MOI was bottlenecked at approximately 0.5. After each infection, nucleic acids were extracted from the clarified culture supernatant using the EZ1 Virus Mini Kit v2 on the EZ1 Biorobot (both from Qiagen). Using two specific real time RT-PCR assays targeting the ΦnsP4 region (see above), the amount of each virus was assessed and the ratio of the two values (WT/re-encoded) was calculated.

Quantification of Intracellular RNA and Viral Proteins

A global estimated MOI of 5 was used to infect confluent 12 well-plates of HEK293 cells with virus stock. Cells were washed once (HBSS) 30 minutes after the infection and 2 ml of media was added. At 8 hours pi, the absence of cytopathic effect was checked, culture supernatants were discarded, and cells were washed once (HBSS). All experiments were performed in triplicate. For Western blot analysis and intracellular viral RNA quantification, total RNA and protein isolation was performed using the same well with the Nucleospin RNA/protein kit according to the manufacturer's instructions (Macherey-Nagel). Protein extracts were resolved on 10% polyacrylamide gels containing SDS and transferred to PVDF membrane. Anti-Nsp1/2 rabbit pAb, anti-actin C-2 mAb (Santa Cruz Biotechnology) and the corresponding HRP-conjugated secondary antibody were used. Protein bands were revealed using Immobilon (Millipore) followed by exposure of blot to radiographic film. Real time RT-PCR assay (see above) was performed to assess viral intracellular RNA (mRNA actin was used as a normalizer to account for differences in cells number and/or quality of extracted RNA as described previously). For the quantification of viral proteins by ELISA, cells were mechanically harvested using a cell scraper, resuspended in 800 μL of PBS, vortexed and disrupted by sonication (30 seconds at 20 KHz, Misonix Sonicator XL). Pre-treated CHIKV-specific immune human serum was used to detect viral proteins.

Experimental Passage of Viruses in Cellulo

The WT and two re-encoded viruses (Φnsp4 and Φnsp1 Φnsp4 Φenv) were passaged 50 times following three regimens: serial passages in Vero or C6/36 cells and alternate passages between Vero and C6/36. For each passage, a 25 cm2 culture flask of confluent cells was infected for 2 hours with the diluted clarified cell supernatant, washed (HBSS) and incubated for 48 hours after the addition of 7 ml of medium. Cell supernatant was then harvested, clarified by centrifugation, aliquoted and stored at −80° C. For each passage, the estimated MOI was bottlenecked at approximately 0.1. To avoid contamination, virus passages were performed in three phases: serial passages of WT and Φnsp4 viruses, alternate passages of the same viruses and passages of the Φnsp1 Φnsp4 Φenv virus. All the viruses passaged at the same time were manipulated sequentially and in different laminar flow cabinets.

Plaque Assay

Monolayers of Vero cells in 12-well culture plates were infected with 1 ml of virus stock (see above). After two hours, cells were washed (HBSS) and 2 ml of 0.9% agarose in culture medium was added. After an incubation of 72 hours, cells were fixed 4 hours with 10% formaldehyde and stained for 30 minutes with a 0.1% naphthalene black solution.

Tissue Culture Infectious Dose 50 (TCID50) Assay

For each determination, a 96-well plate culture of confluent Vero cells was inoculated with 150 μl/well of serial 10-fold dilutions of centrifugation clarified cell culture supernatants: each row included 6 wells of the dilution and two negative controls. The plates were incubated for 7 days and read for absence or presence of CPE in each well. The determination of the TCID50/ml was performed using the method of Reed and Muench. When the value obtained with a sample was less than the detection threshold of the method (101.82 TCID50/ml), the inventors performed another assay with twofold, 20-fold and 200-fold dilutions (detection threshold: 101.13 TCID50/ml). Values lower than this threshold were considered equal to 101.13 TCID50/ml in the graphic presentations and were not taken into account in the statistical analyses. Assuming that the re-encoding and/or the experimental passages could modify significantly the appearance of CPE, the inventors used a qRT-PCR assay (see below) as a sensitive indicator of the presence of infectious virus. This assay was performed for each virus (first passage and when available, 25th and 50th passages). For all the viruses, CPE positive wells were positive in qRT-PCR with a threshold cycle lower than 16 while those that failed to produce CPE were negative or positive with a threshold cycle >35, the value expected after the dilution of the initial RNA yields.

Haemagglutination Assay

An estimated MOI of 5 was used to infect with virus stock (see above) a 25 cm2 culture flask of confluent Vero or C6/36 cells. Cells were washed twice (HBSS) 30 minutes after the infection and 8 ml of medium without FBS was added. 2 ml of cell supernatant was sampled at 16 hours pi. Sampled supernatants were clarified by centrifugation, aliquoted and stored at −80° C. They were then analysed using a TCID50 assay (see above), a real time RT-PCR assay and a haemagglutination titration assay was performed using standard methods: twofold serial dilutions of cell supernatant on U-bottom microplates were prepared in 0.4% bovine albumin/borate saline pH 9.0 solution (final volume: 35 μl per well). Thirty-five microliters of pre-diluted goose red blood cells (1/150 using the final pH 6.0 adjusting diluents) were added, the mixture was homogenized, incubated for 45 min at room temperature and then read using four scoring symbols: ++ for complete haemagglutination, + for partial haemagglutination, +/− for trace haemagglutination and − for negative haemagglutination. The haemagglutination titre was the reciprocal of the highest dilution in which + was observed.

Results

The inventors have evaluated the effect on replicative fitness and cytopathogenicity of large-scale re-encoding of CHIKV, a re-emerging Old World pathogenic arbovirus. The generation of attenuated viruses by large-scale re-encoding represents an exciting and potentially important route to vaccine development, and also to understanding the basis of the evolution of viral pathogenicity. Site-directed re-encoding, associated with no modification of amino acid sequences, alleviates the likelihood of novel phenotypic properties, allows us to modulate fitness by altering the length of the codon replacement interval, but additionally provides benefits to the generic development of live attenuated vaccines, including reduced costs and single dose induction of long-term immunity.

A key result was the observation that the random re-encoding method disclosed herein decreased the replicative fitness of CHIKV in both primate and arthropod cells. The diminution of CHIKV replicative fitness correlated directly with the degree of re-encoding. The inventors found that during one replicative cycle in mosquito cells, codon re-encoding profoundly reduced the infectious titre of released virus whilst the number of viral particles remained stable. This implies that the maturation process (i.e. the formation of ribonucleoproteins and their insertion into plasma membranes that contain HA) could be at fault when viruses are re-encoded.

In contrast, in primate cells, this decline in infectivity of the viral particles was associated with the reduced generation of viral RNA and proteins probably due to a compromised replication complex.

These results indicate that synonymous mutations in viral genomes have major fitness effects and not only in the small number of cis-acting elements described previously (Gerardin et al., 2008).

Indeed, during this experiment, six re-encoded viruses were produced of which the most re-encoded virus modified in three regions that encode different proteins (together, 882 synonymous mutations were introduced spanning 4,212 nt). In support of previous studies which demonstrated that re-encoded poliovirus and influenza A viruses are attenuated, the observation of a reduction in replicative fitness strongly suggest that a proportion of synonymous mutations are not neutral in RNA viruses. Indeed, it is likely that some synonymous mutations were positively selected during the passaging process, reinforcing the idea that synonymous sites are central to viral fitness. In conclusion, it is likely that synonymous mutations can be either neutral, beneficial or deleterious as is the case for non-synonymous mutations.

Evolutionary patterns at synonymous sites could be shaped by genome-wide mutational processes, such as G+C %, codon usage bias and dinucleotide frequency. These global constraints, which theoretically produce a subset of viable genomes, were assessed by previous studies of codon re-encoding in poliovirus, influenza A virus and bacterial virus T7 which applied specific modification of codon usage bias, codon pair bias or CpG/UpA frequencies.

Using a large-scale random re-encoding method, which only slightly modified these global properties, the inventors still observed replicative fitness reductions in both primate and arthropod cells. These results indicate that local constraints may also provide significant selection pressure on synonymous sites in RNA viruses, for example by disrupting RNA secondary structures. Since numerous functional secondary structures are present in coding regions of RNA viruses, and hence include synonymous sites (with notable examples in poliovirus, tick-borne encephalitis virus, alphaviruses and HIV-1), it is likely that similar structures are common in CHIKV.

Recently, it was demonstrated that a similar re-encoding strategy applied to the noncapsid regions of the poliovirus resulted in the identification of two novel functional RNA elements. The concept of large-scale random re-encoding, as described here, is also supported by the report of the negative impact of random single synonymous mutations (which did not modify the genetic characteristics of the genome) on viral replicative fitness.

Finally, these results indicate that the reduction of viral replicative fitness is driven by a variety of factors.

First, the nature of the virus studied is an important parameter: the inventors found that introducing up to 882 random synonymous mutations clearly affected the replicative fitness of the CHIKV, whilst two previous studies demonstrated that comparable random re-encoding methods applied to the capsid precursor (P1) region of the poliovirus did not significantly affect replicative fitness (934 and 153 synonymous substitutions were introduced, respectively).

The location of the re-encoded region constitutes the second factor of importance: re-encoding in the E2/E1 region resulted in a greater loss of fitness than in other genomic regions. The analysis of complete wild type CHIKV genomes revealed naturally low levels of synonymous diversity in this re-encoded region indicating that this region is subject to specific local evolutionary constraints which in part explain the significant impact of re-encoding in this region.

The average impact of one mutation is clearly likely to be less important in random re-encoding than in specific approaches. This suggests that random large-scale re-encoding could be advantageous in several aspects when designing future vaccine candidates, namely:
  (i) reversion to wild-type should be intrinsically more difficult, given the high number of mutations produced;
  (ii) since in the present experiments the reduction of replicative fitness decreased with the degree of re-encoding, the method opens the door to finely tuning fitness reduction through modulation of the length of re-encoded regions and the number of synonymous mutations introduced;
  (iii) the use of a combination of several re-encoded regions located throughout the viral genome may prevent complete phenotypic reversion due to recombination between WT and re-encoded viruses: large scale sequence modification may render recombination intrinsically more difficult, and in the case of recombination, the part of the genome representing the re-encoded strain would likely still carry some mutations associated with fitness reduction.

Consequently these re-encoded viruses are very stable. To corroborate, the inventors passaged the wild type and two re-encoded CHIKVs in cellulo. During serial passage of the re-encoded viruses, the inventors observed that the response to codon re-encoding and adaptation to culture conditions occurred simultaneously. However, the high levels of observed convergent evolution between the WT virus and the re-encoded viruses indicates that selection arising from codon re-encoding was likely weaker than that for adaptation to culture conditions, and/or that the beneficial mutations to restore the cost of re-encoding were less likely to arise. Therefore, this indirect insight into the difficulty of reversing the effects of re-encoding further highlights the stability of these re-encoded viruses.

These experiments also confirm that mutations acquired in one host can be deleterious in a different host type (serial passages in primate cells increased viral replicative fitness in primate cells, whilst serial passages in mosquito cells decreased viral fitness in primate cells) and, with the exception of the most re-encoded virus, that alternate passages seriously (i) limit replicative fitness enhancement, and (ii) delay the appearance of the mutations.

In conclusion, these experiments demonstrate that random codon re-encoding significantly decreases the replicative fitness of CHIKV. Although all these results are important and encouraging, they cannot be easily extended to RNA viruses producing chronic infections. Thus, studies in animal models are obviously needed to evaluate the potential of these new generation attenuation methods for producing vaccine candidates. However, this approach could assist in the development of future RNA virus vaccines, including those for arboviruses. Introducing a large number of slightly deleterious synonymous mutations reduced the replicative fitness of CHIKV by orders of magnitude in both primate and arthropod cells. This strategy resulted in limited reversion and recovery of fitness after intensive serial subculture of the viruses, and is likely to reduce the risk of complete phenotypic reversion if recombination with wild type virus occurs. Our results encourage us that such modified viruses would find it difficult to return to their natural arboviral cycle in the real world. Furthermore, the decrease of the replicative fitness correlated with the extent of re-encoding, an observation that may be advantageous in the development of future strategies to modulate viral attenuation.

Example 3: Attenuation of Further RNA Viruses

The large scale codon re-encoding step of the invention has been shown to be a powerful method of attenuation which has several advantages for vaccine development, including the possibility to obtain potential vaccine strains in a very short period as soon as the complete sequence of the targeted pathogen is known and an infectious genome can be produced. It also has the possibility to modulate precisely the degree of replicative fitness loss and to generate safe, live-attenuated vaccines that confer long-term protection, in a cost effective manner.

The inventors applied the method of attenuation disclosed herein and exemplified in example 2, to 2 other arboviruses (both are flaviviruses; enveloped single-strand positive-sense RNA viruses): the Tick-Borne Encephalitis Virus (TBEV) and the Japanese encephalitis virus (JEV).

A) TBEV

Following the method of large-scale codon re-encoding previously applied to the Chikungunya virus (CHIKV), the inventors modified the NS5 genomic region (a cassette of 1412 pb, as depicted in SEQ ID No: 66) of the TBEV (Oshima 5-10 strain), inserting 273 silent mutations (random codon re-encoding).

The TBEV strain Oshima 5-10, which was isolated in 1995 in Japan, belong to the Far Eastern subtype and shows an important virulence in mice (it provokes encephalitis as for humans). Wild-type (WT) and NS5_random_re-encoded viruses are obtained using the ISA method and classical methods (infectious clones were obtained). The replicative fitness of the corresponding viruses was measured in cellulo and was almost identical.

TABLE 4

Genetic characteristics of the studied TBEV

| Virus | Cassette size (NS5 genomic region) | Number of mutations | ENC of the complete open reading frame | % G + C of the complete open reading frame |
|---|---|---|---|---|
| WT | — | — | 54.0 | 54.3 |
| NS5 re-encoded | 1412 nt | 273 | 55.5 | 53.8 |

Codon usage was measured using the effective number of codons ENC which gives a value ranging from 20 (only one codon used for each amino acid) to 61 (random codon usage for each amino acid).

An in vivo model was then used to measure the attenuation phenotype of this re-encoded TBEV. After intraperitoneal inoculation ($2 \cdot 10^4$, $2 \cdot 10^5$ and $2 \cdot 10^6$ TCID50 of viruses were used), mice were monitored for symptom appearance and weighted every day during 20 days.

Results show a delay weight loss and symptom appearance for mice infected with NS5_random_re-encoded virus compare to those infected by WT virus. Moreover, the number of mice displaying at least one symptom, weight loss ($\leq 94\%$) and virus in the brain (detection of viral RNA by real time RT-PCR) is significantly higher for WT infected mice than NS5_random_re-encoded infected mice. High levels of seroneutralising IgG antibodies were observed in mice infected with NS5_random_re-encoded virus at 30 days after the first inoculation. Finally, challenge experiments (mice were challenged 30 days after the first inoculation) by the WT virus show that all the mice previously infected by re-encoded viruses were protected (based on appearance of symptoms and weight loss).

TABLE 5

Genetic characteristics of the different WT, lightly or strongly re-encoded fragments.

| | Fragment I | | | Fragment II | | | Fragment III | | |
|---|---|---|---|---|---|---|---|---|---|
| Virus | Length | Mutation | G + C % | Length | Mutation | G + C % | Length | mutation | G + C % |
| WT | 3646 | — | 50.8 | 2854 | — | 52.3 | 3410 | — | 53.0 |
| 500 | 3646 | 225 (6.2%) | 49.7 | 2854 | 161 (5.6%) | 51.6 | 3410 | 199 (5.8%) | 52.0 |
| 1500 | 3646 | 672 (18.4%) | 49.1 | 2854 | 482 (16.9%) | 49.6 | 3410 | 563 (16.5%) | 50.3 |

Number of the fragment (first, second or third), length, number of synonymous mutations and G+C % are indicated. 500 and 1500 mean low and high level of re-encoding.

Using the reverse genetics method ISA and combinations of these WT and re-encoded fragments, the inventors produced a large number of recombinant viruses harboring gradual levels of re-encoding in different parts of the genome.

B) JEV

The inventors have modified the JEV strain 'JEV_CNS769_Laos_2009' (Genotype 1) using the large scale random codon re-encoding method.

A different approach is used here: the inventors re-encoded in silico almost all the complete open reading frame (ORF), from the beginning of PrM to the end of NS5 genomic regions, using two different levels of re-encoding: a high level and a low level of re-encoding with the insertion of either 585 or 1717 synonymous mutations throughout the open reading frame (FIG. 3).

For his purposes, the inventors used at least one re-encoded cassette as depicted in SEQ ID No: 67; SEQ ID No: 68; SEQ ID No: 69; SEQ ID No: 70; SEQ ID No: 71; and SEQ ID No:72.

In cellulo replicative fitness of these re-encoded JEVs was measured using human cells: Preliminary results show a decrease of the replicative fitness according to the level of re-encoding, the size of the re-encoding region and the genomic position of the re-encoded fragment(s) (FIG. 4).

Example 4: In Vivo Generation

Overlapping fragments covering the entire genome of RNA viruses and flanked respectively at 5 and 3' by promoter of DNA-dependent RNA polymerase and terminator/RNA polyadenylation signal were prepared using the method of the invention.

These DNA fragments were directly inoculated to live animals and allowed to recover infectious virus from several animal samples. In addition, clinical surveillance of animals (appearance of symptom and significant weight loss) allowed to observed typical signs of infection.

a) Experiment 1: Tick-Borne Encephalitis Virus (TBEV; Flavivirus)

The inventors used a wild-type strain of tick-borne encephalitis virus (strain Oshima 5.10 (GenBank accession number AB062063)). They applied the method of the invention to DNA overlapping fragments.

Five-weeks-old C57Bl/6J female mice were inoculated with three DNA overlapping fragments.

The clinical course of the viral infection was monitored by following (i) the clinical manifestations of the disease (shivering, humpback, dirty eyes, hemi- or tetra-paresia, hemiplegia or tetraplegia); and (ii) the weight of the mice exactly as described by Fabritus L et al., 2015, Attenuation of Tick-Borne Encephalitis Virus Using Large-Scale Random Codon Re-encoding. PLoS Pathog 11(3).

Brains and spleens were collected from sacrificed mice 14 days post-inoculation.

Brains and spleens were grounded and centrifuged. The resulting supernatant was used to assess the presence of infectious virus.

The presence of infectious virus was assessed using molecular (real time RT-PCR) and classical cell culture methods (isolation of infectious viruses).

Using an initial amount of DNA ranging between 2 to 5 µg, and two different inoculation routes (intraperitoneal and intradermal injections), infectious viruses were detected from both brains and spleens. Clinical manifestations (significant weight losses and symptoms) of the diseases were also observed.

b) Experiment 2: Intracerebral Inoculation of Suckling Mice

The inventors used wild-type strains of tick-borne encephalitis virus (strain Oshima 5.10 (GenBank accession number AB062063)) and Japanese encephalitis (JEV_CNS769_Laos_2009 (GenBank accession number KC196115)). They used the method of the invention to generate the DNA overlapping fragments.

DNA overlapping fragments were used diluted in PBS or were mixed with a transfection reagent.

Suckling OF1 mice were inoculated by intracerebral injection of DNA overlapping fragments. The clinical course of the viral infection was monitored by following the clinical manifestation of the disease (shivering, lethargy). Brains were collected from sacrificed mice 6-12 days post-inoculation. Brains were grounded and centrifuged. The resulting supernatant was used to assess the presence of infectious virus.

The presence of infectious virus was assessed using molecular (real time RT-PCR) and classical cell culture methods (isolation of infectious viruses).

Using 2 μg of DNA, infectious viruses were detected in brains for both viruses (TBEV and JEV) and with or without addition of transfection reagent. Clinical manifestations of the diseases were also observed.

CONCLUSION

The inventors have thus harnessed the power of the methods disclosed herein by generating virus in vivo. Sais method would thus be highly efficient for developing a live attenuated vaccine in vivo, i.e. directly within the body a subject.

The invention claimed is:

1. A method for generating an attenuated RNA virus comprising:
   A) re-encoding the viral genome of an infectious RNA virus by randomly substituting a part of the nucleotide codons of the entire viral genome of said infectious RNA virus by another nucleotide codon encoding for the same amino acid,
   with the proviso that:
      i) the number and position of rare nucleotide codons present in said viral genome are not modified, said rare nucleotide codons being CGU, CGC, CGA, CGG, UCG, CCG, GCG and ACG; and
      ii) the regions of said viral genome which are involved with RNA secondary structure are not modified;
   B) generating an attenuated RNA virus by:
      i) introducing a promoter of DNA-dependent RNA polymerase in position 5' and optionally a terminator and a RNA polyadenylation sequence in position 3' of the re-encoded viral genome as obtained in step A;
      ii) amplifying the re-encoded viral genome as prepared in sub-step B) i) including said promoter and optionally said terminator and RNA polyadenylation sequence, in at least 2 overlapping cDNA fragments;
      iii) transfecting said cDNA fragments into a host cell;
      iv) incubating said host cell of sub-step B) iii); and
      v) recovering the attenuated RNA virus from said incubated host cell.

2. The method of claim 1, wherein in step A, about 1% to about 20% of the nucleotide codons of the entire viral genome of said infectious RNA virus are substituted by another nucleotide codon encoding for the same amino acid.

3. The method of claim 1, wherein step A is performed by:
   determining the amino acid sequence encoded by the entire viral genome of the infectious RNA virus, and determining each nucleotide codon encoding each amino acid; and
   substituting 1% to 20% of the nucleotide codon of the viral genome encoding an amino acid of table 1, by a different nucleotide codon encoding the same amino acid as specified in the following table:

| Amino acid | Nucleotide codon |
|---|---|
| Ala, A | GCU, GCC, GCA |
| Arg/R | AGA, AGG |
| Asn/N | AAU, AAC |
| Asp/D | GAU, GAC |
| Cys/C | UGU, UGC |
| Gln/Q | CAA, CAG |
| Glu/E | GAA, GAG |
| Gly/G | GGU, GGC, GGA |
| His/H | CAU, CAC |
| Ile/I | AUU, AUC, AUA |
| Leu/L | UUA, UUG, CUU, CUC, CUA, CUG |
| Lys/K | AAA, AAG |
| Phe/F | UUU, UUC |
| Pro/P | CCU, CCC, CCA |
| Ser/S | UCU, UCC, UCA, AGU, AGC |
| Thr/T | ACU, ACC, ACA |
| Tyr/Y | UAU, UAC |
| Val/V | GUU, GUC, GUA, GUG. |

4. The method of claim 1, wherein said virus is a single stranded positive RNA virus.

5. The method of claim 1, wherein, in step B) i),
   said promoter of DNA-dependent RNA polymerase in position 5' is the human cytomegalovirus promoter (pCMV); and/or
   said optional terminator and RNA polyadenylation sequence is respectively the hepatitis delta ribozyme and the simian virus 40 polyadenylation signal (HDR/SV40pA).

6. The method of claim 1, wherein:
   step B) iii) is a step of direct transfection of the cDNA fragments obtained in step B) ii), and
   said step B) iii) occurs directly after step B) ii).

7. The method of claim to 1, wherein step B) iii) is a step of transfection of plasmids or vectors comprising a cDNA fragment obtained in step B) ii), wherein each cDNA fragment is in individual and separate plasmid or vector.

8. The method of claim 1, wherein the transfected cDNA fragments of step B) iii) spontaneously recombine in the host cells during the incubation step B) iv).

9. The method of claim 1, wherein said virus is Chikungunya virus and said step A of re-encoding is performed:
   in the region coding for the non-structural protein nsP1, wherein the re-encoded cassette is depicted in SEQ ID NO: 63;
   in the region coding for the non-structural protein nsP4, wherein the re-encoded cassette is depicted in SEQ ID NO: 64; and
   in the region coding for the region overlapping the structural protein E2 and E1, wherein the re-encoded cassette is depicted in SEQ ID NO: 65.

10. The method of claim 1, wherein said virus is Tick-borne encephalitis virus and said step A of re-encoding step is performed in the NS5 genomic region, wherein the re-encoded cassette is depicted in SEQ ID NO: 66.

11. The method of claim 1, wherein said virus is Japanese encephalitis virus and said step A is performed in the complete open reading frame (ORF), from the beginning of PrM to the end of NS5 genomic region, wherein at least one re-encoded cassette is selected from the group consisting of SEQ ID NO: 67; SEQ ID NO: 68; SEQ ID NO: 69; SEQ ID NO: 70; SEQ ID NO: 71; and SEQ ID NO:72.

12. The method of claim 1 wherein said method produces a live attenuated vaccine.

13. The method of claim 4, wherein said virus is a virus selected from the group consisting of flavivirus, alphavirus and enterovirus.

\* \* \* \* \*